United States Patent
Eberle et al.

[11] Patent Number: 5,547,919
[45] Date of Patent: Aug. 20, 1996

[54] α-PYRIMIDINYL ACRYLIC ACID DERIVATIVES

[75] Inventors: Martin Eberle, Bottmingen; Fritz Schaub, Aesch; Gerald W. Craig, Basel, all of Switzerland

[73] Assignee: Sandoz Ltd., Basel, Switzerland

[21] Appl. No.: 370,992

[22] Filed: Jan. 10, 1995

[30] Foreign Application Priority Data

Jan. 18, 1994 [GB] United Kingdom ............... 9400889

[51] Int. Cl.$^6$ .................... C07D 239/02; A01N 43/54
[52] U.S. Cl. .................... 504/242; 504/243; 544/319
[58] Field of Search ............... 544/319; 504/242, 504/243

[56] References Cited

FOREIGN PATENT DOCUMENTS

| | | | |
|---|---|---|---|
| 243012 | 3/1987 | European Pat. Off. | C07D 213/63 |
| 299694 | 7/1988 | European Pat. Off. | C07D 277/74 |
| 312221 | 9/1988 | European Pat. Off. | C07D 213/64 |
| 312243 | 10/1988 | European Pat. Off. | C07D 213/64 |
| 383117 | 2/1990 | European Pat. Off. | C07D 213/74 |
| 471261 | 8/1991 | European Pat. Off. | C07D 239/42 |
| 471262 | 8/1991 | European Pat. Off. | C07D 277/42 |
| 634405 | 7/1994 | European Pat. Off. | C07D 239/34 |

*Primary Examiner*—Sharon Gibson
*Assistant Examiner*—Catherine Kilby Scalzo
*Attorney, Agent, or Firm*—Lynn Marcus-Wyner; Allen E. Norris

[57] ABSTRACT

The invention discloses compounds of formula I

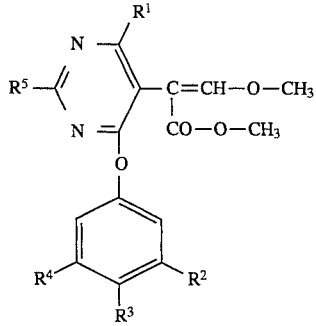

the use of such compounds for the control of phytopathogens, composition for facilitating such use, and the preparation of the compounds of formula I.

11 Claims, No Drawings

α-PYRIMIDINYL ACRYLIC ACID DERIVATIVES

This invention relates to novel α-pyrimidinyl acetic acid derivatives, the synthesis thereof and the use of said compounds for the control of phytopathogens.

α-(Pyrid-3-yl)-β-methoxy acrylates are known from EP-A-0 243 012. Said compounds have been proposed as agricultural/horticultural fungicides.

It has now been found that 2-(4-phenoxypyrimidin-5-yl)-acetic acid derivatives of formula I

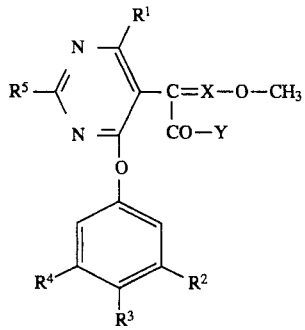

wherein
$R^1$ is $C_{1-4}$alkoxy or -$NR^8R^9$,
$R^2$ is $C_{1-4}$alkyl, $C_{1-4}$haloalkyl, aryl, aryloxy, $C_{3-5}$alkenyloxy, $C_{3-5}$alkynyloxy, halogen, aryl-$C_{1-4}$alkoxy, aryloxy-$C_{1-4}$alkyl, aryloxy-$C_{1-4}$alkoxy, aryl-$C_{3-5}$alkenyloxy, heteroaryl, heteroaryloxy, $C_{1-4}$alkoxy, $C_{2-5}$alkenyl, $C_{2-5}$alkynyl, $C_{1-4}$alkoxycarbonyl, -$CONR^{10}R^{11}$, -O-$CONR^{10}R^{11}$, -$CR^7$=N-$NR^6R^{12}$ -$CR^7$=N-O-$R^6$ or a group

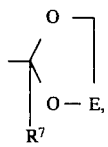

$R^3$ is hydrogen, $C_{1-4}$alkyl, $C_{1-4}$alkoxy, cyano, nitro or halogen,
$R^4$ is hydrogen, halogen, $C_{1-4}$alkoxy or $C_{1-4}$alkyl,
$R^5$ is hydrogen or methyl,
$R^6$ is $C_{1-12}$alkyl, $C_{3-12}$alkenyl, $C_{3-12}$alkynyl, aryl-$C_{1-4}$alkyl, aryl or heteroaryl,
$R^7$ is hydrogen or methyl,
$R^8$ and $R^9$ are independently $C_{1-4}$alkyl or together $C_{3-6}$alkylene,
$R^{10}$ and $R^{11}$ are independently $C_{1-4}$alkyl or together $C_{3-6}$alkylene or $C_{3-6}$alkylene interrupted by oxygen or sulfur,
$R^{12}$ is hydrogen or methyl,
E is $C_{1-3}$alkylene,
X is CH or nitrogen, and
Y is $OCH_3$, $NH_2$, $NHCH_3$ or $N(CH_3)_2$;
am suprisingly effective against phytopathogens.

In the definitions of the radicals of formula I alkyl is understood to encompass straight-chain and branched alkyl groups, with branched-chain and lower alkyl being preferred. For example alkyl is methyl, ethyl, n-propyl, isopropyl, n-butyl, isobutyl, tertiary butyl or secondary butyl. Alkoxy for example encompasses methoxy, ethoxy, n-propoxy, isopropoxy, n-butyloxy, isobutyloxy, tertiary butyloxy or secondary butyloxy. Halogen designates fluorine, chlorine, bromine and iodine, with fluorine and chlorine being preferred. Haloalkyl designates straight chain or branched alkyl groups which are mono- to perhalogenated with straight-chain lower alkyl being the preferred alkyl and with fluorine and chlorine being preferred halogens. Examples are trifluoromethyl, difluoromethyl, 2,2,2-trifluoroethyl or 2,2,3,3,3-pentafluoropropyl. Aryl stands for aromatic hydrocarbon radicals, for example phenyl, naphthyl or anthracenyl, with phenyl being preferred. The aryl radical may optionally be further substituted. Aryloxy designates an aryl radical being bounded through an oxygen atom. Examples are phenoxy, naphthyloxy or anthracenyloxy. The aryloxy radical may optionally be further substituted at the aryl part. Alkenyloxy designates for example allyloxy, 2-butenyloxy, 3-butenyloxy, 2-pentenyloxy, -methallyloxy, 3-pentenyloxy, 4-pentenyloxy, 2-methyl-2-butenyloxy, 3-methyl- 2-butenyloxy, or 3-methyl-3-butenyloxy. Alkynyloxy is for example propargyloxy, 2-butynyloxy, 3-butynyloxy, 2-pentynyloxy, 3-pentynyloxy, 4-pentynyloxy, 2-methyl- 3-butynyloxy or 1-methylpropargyloxy. Arylalkoxy is for example benzyloxy, 2-phenylethoxy or 1-phenylethoxy or 3-phenylpropoxy. The arylalkoxy may optionally be further substituted at the aryl part. The alkylene bridge formed by $R^4$ and $R^5$ together may be straight chain or branched. Examples are -$(CH_2)_3$-,-$(CH_2)_4$-, -$(CH_2)_5$-, or -$CH_2$-$CH_2$-$CH(CH_3)$-$CH_2$-. The alkylene chain designated by E is for example -$CH_2$-, -$CH_2$-$CH_2$-, -$C(CH_3)_2$-, or -$CH(CH_3)$-. Examples for aryloxyalkoxy are phenoxymethoxy, 1-phenoxyethoxy, 2-phenoxyethoxy, 3-phenoxypropoxy or 2-phenoxypropoxy. The aryloxyalkoxy may optionally be further substituted at the aryl part. Examples for arylalkenyloxy are 3-phenylallyloxy, or 3-phenylmetallyloxy. The arylalkenyloxy may optionally be further substituted at the aryl part. Aryloxyalkyl or heteroaryloxyalkyl designate an aryl or heteroaryl radical being linked to the alkyl chain through an oxygen atom. Typical examples are phenoxymethyl, phenoxyethyl or phenoxypropyl. The aryloxyalkyl or heteroaryloxyalkyl may optionally be further substituted at the aromatic ring. Alkenyl designates for example vinyl, allyl, 2-butenyl, 3-butenyl, 2-pentenyl, 2-methallyl, 3-pentenyl, 4-pentenyl, 2-methyl-2-butenyl, 3-methyl-2-butenyl, or 3-methyl- 3-butenyl. Alkynyl is for example ethynyl, propargyl, 2-butynyl, 3-butynyl, 2-pentynyl, 3-pentynyl, 4-pentynyl, 2-methyl-3-butynyl or 1-methylpropargyl. Heteroaryl stands for aromatic 5- or 6-membered cyclic radicals comprising one, two or three ring atoms selected from nitrogen, oxygen and sulfur, which may also be in condensed form with another heteroaryl radical or aryl radical. Examples are pyridyl, pyrimidinyl, thienyl, oxazolyl, oxadiazolyl, triazolyl, thiadiazolyl, furyl, isoxazolyl, thiazolyl, imidazolyl, pyrazolyl, benzothiazolyl, benzoxazolyl and the like. Heteroaryloxy designates a heteroaryl radical being linked through an oxygen bridge. The alkylene bridges optionally formed by $R^8$ and $R^9$ or $R^{10}$ and $R^{11}$, respectively, together with the nitrogen atom to which they are attached form e.g. a pyrrolidinyl or piperidinyl radical bound through the nitrogen atom. Where the alkylene chain is interrupted by oxygen or sulfur the group $NR^{10}R^{11}$ may e.g. stand for N-morpholinyl or N-thiomorpholinyl. Examples for alkoxycarbonyl are e.g. methoxycarbonyl, ethoxycarbonyl or propoxycarbonyl.

In radicals being combined from various other definitions, each of the definitions has the meanings given for the partial definition separately.

The above aryl and heteroaryl radicals may be further substituted. Where aryl or heteroaryl is substituted, it is preferably substituted by one or two radicals selected from the group comprising halogen, $C_{1-4}$alkyl, $C_{1-4}$alkoxy, $C_{1-4}$haloalkyl, $C_{1-4}$haloalkoxy, cyano, nitro, phenyl or phenoxy, which phenyl or phenoxy radicals may in turn be substituted with one or two radicals selected from halogen, $C_{1-4}$alkyl, $C_{1-4}$alkoxy, $C_{1-4}$haloalkyl, cyano or nitro.

Preferred subgroups of the compounds of formula I are those wherein either a) $R^1$ is methoxy or dimethylamino, or
b) $R^2$ is phenyl, phenoxy, $C_{1-4}$alkyl, $-C(CH_3)=N-O-R^6$ or $CF_3$, or is thiazolyl or isoxazolyl each optionally substituted by phenyl, $C_{1-4}$alkyl or $CF_3$ wherein $R^6$ is $C_{1-6}$alkyl or allyl, or benzyl or 2-phenylethyl, each optionally substituted at the phenyl ring with $C_{1-4}$alkyl, $C_{1-4}$alkoxy, halogen or $CF_3$; or
c) $R^3$ is hydrogen, or
d) $R^4$ is hydrogen or methyl, or
e) $R^5$ is hydrogen or methyl.

In a more preferred subgroup of compounds of formula I $R^1$ is methoxy or dimethylamino, $R^2$ is phenyl, phenoxy, $C_{1-4}$alkyl, $-C(CH_3)=N-O-R^6$ or $CF_3$, or is thiazolyl or isoxazolyl each optionally substituted with phenyl, $C_{1-4}$alkyl or $CF_3$, $R^3$ is hydrogen, $R^4$ is hydrogen or methyl and $R^5$ is hydrogen or methyl, wherein $R^6$ is $C_{1-6}$alkyl or ally, or benzyl or 2-phenylethyl each optionally substituted at the phenyl ring with $C_{1-4}$alkyl, $C_{1-4}$alkoxy, halogen or $CF_3$.

Preferred individual compounds of formula I are:

Methyl α-[4-(3-methyl-5-isopropylphenoxy)-6-methoxy-pyrimidin- 5-yl]-β-methoxyacrylate;

Methyl α-[4-(3-tert.butylphenoxy )-6-methoxy-pyrimidin-5-yl]-β-methoxyacrylate;

Methyl α-[4-(3-tert.butylphenoxy)-6-dimethylamino-pyrimidin-5-yl]-β-methoxyacrylate;

Methyl α-[4-(3-isopropylphenoxy)-6-methoxy-pyrimidin-5-yl]-β-methoxyacrylate;

Methyl α-[4-(3-trifluoromethylphenoxy )-6-methoxy-pyrimidin-5-yl]-β-methoxyacrylate;

Methyl α-[4-(3-phenoxyphenoxy)-6-methoxy-pyrimidin-5-yl]-β-methoxyacrylate:

Methyl 2-[4-(3-( 1 -(3-chlorobenzyloximino)-ethyl)-phenoxy)-6-dimethylamino-pyrimidin- 5-yl]-2-methoximino-acetate;

Methyl 2-[4-(3-(1-ethoximino)-ethyl)-phenoxy)-6-dimethylamino-pyrimidin-5-yl]- 2-methoximino-acetate;

Methyl α-[4-(3-(1-methoximino)-ethyl)-phenoxy)-6-methoxy-2-methyl-pyrimidin-5-yl]-β-methoxyacrylate;

Methyl α-[4-(3-trifluoromethylphenoxy )-6-methoxy-2-methyl-pyrimidin-5-yl]-β-methoxyacrylate;

Methyl 2-[4-(3-(1 -ethoximino)-ethyl)-phenoxy)-6-dimethylamino-2-methyl-pyrimidin-5-yl]- 2-methoximino-acetate;

Methyl 2-[4-(3-(1 -(2,5-dimethylbenzyloximino)-ethyl)-phenoxy)-6-dimethylamino-pyrimidin- 5-yl]-2-methoximino-acetate;

Methyl 2-[4-(3-(1 -(3-chlorobenzyloximino)-ethyl)-phenoxy)-6-dimethylamino- 2-methyl-pyrimidin-5 -yl)-2-methoximino-acetate;

Methyl 2-[4-(3-(1-(2,5-dimethylbenzyloximino)-ethyl)-phenoxy)- 6-dimethylamino-2-methyl-pyrimidin-5-yl]-2-methoximino-acetate;

Methyl 2-[4-(3-(1 -(2,5-dichlorobenzyloximino)-ethyl)-phenoxy)-6-dimethylamino- 2-methyl-pyrimidin-5-yl]-2-methoximino-acetate;

Methyl α-[4-(3-(1-(2,5-dimethylbenzyloximino)-ethyl)-phenoxy)-6-methoxy- 2-methyl-pyrimidin-5-yl]-β-methoxyacrylate;

Methyl α-[4-(3-(1-(3-chlorobenzyloximino)-ethyl)-phenoxy)-6-methoxy- 2-methyl-pyrimidin-5-yl]-β-methoxyacrylate;

Methyl α-[4-(3-(1-(2,5-dimethylbenzyloximino)-ethyl)-phenoxy)- 6-methoxy-pyrimidin-5-yl]-β-methoxyacrylate;

Methyl 2-[4-(3-(1 -(3-chlorobenzyloximino)-ethyl)-phenoxy)-6-methoxy-pyrimidin-5-yl]-2-methoximino-acetate;

Methyl 2-[4-(3-(3-trifluoromethylisoxazol-5-yl)-phenoxy)-6-dimethylamino-pyrimidin-5-yl]-2-methoximino-acetate;

Methyl 2-[4-(3-phenylphenoxy )-6-dimethylamino-pyrimidin-5-yl]-2-methoximino-acetate;

Methyl 2-[4-(5-methyl-3-isopropyl-phenoxy)-6-dimethylamino-pyrimidin-5-yl]-2-methoximino-acetate;

Methyl 2-[4-(5-methyl-3-isopropyl-phenoxy)-6-dimethylamino-2-methyl-pyrimidin-5-yl]-2-methoximino-acetate;

Methyl 2-[4-(3-(2-methylbenzyloxy)-phenoxy )-6-dimethylamino-pyrimidin-5-yl]-2-methoximino-acetate;

Methyl 2-[4-(3-(2-methylbenzyloxy)-phenoxy )-6-dimethylamino-2-methyl-pyrimidin-5-yl]-2-methoximino-acetate;

Methyl 2[4-(3-phenylethoxy)-phenoxy)-6-dimethylamino-pyrimidin-5-yl]- 2-methoximino-acetate;

Methyl 2-[ 4-(3-phenylethoxy)-phenoxy)-6-dimethylamino-2-methyl-pyrimidin-5-yl]-2-methoximino-acetate;

Methyl 2-[4-(3-(2-phenylthiazol-4-yl)-phenoxy )-6-dimethylamino-pyrimidin-5-yl]-2-methoximino-acetate;

Methyl 2-[4-(3-(2-phenylthiazol-4-yl)-phenoxy )-6-dimethylamino-2-methyl-pyrimidin- 5-yl]-2-methoximino-acetate;

Methyl 2-[4-(3-(3-trifluoromethylisoxazol-5-yl)-phenoxy)-6-dimethylamino- 2-methyl-pyrimidin-5-yl]-2-methoximino-acetate;

Methyl 2-[4-(3-phenylphenoxy)-6-dimethylamino-2-methyl-pyrimidin-5-yl]- 2-methoximino-acetate;

N-methyl 2-[4-(3-phenylphenoxy)-6-dimethylamino-2-methyl-pyrimidin-5-yl]-2-methoximino-acetamide;

Methyl α-[4-(3-phenylphenoxy )-6-dimethylamino-2-methyl-pyrimidin-5-yl]-β-methoxyacrylate;

Methyl α-[4-(3-(3-trifluoromethylisoxazol-5-yl)-phenoxy) -6-methoxy-pyrimidin-5-yl]-β-methoxyacrylate;

Methyl α-[4-(3-(3-trifluoromethylisoxazol-5-yl)-phenoxy)-6-methoxy-2-methyl-pyrimidin- 5-yl]-[3-methoxyacrylate;

Methyl α-[4-(5-methyl-3-isopropylphenoxy)-6-methoxy-2-methyl-pyrimidin-5-yl]-β-methoxyacrylate; and Methyl α-[4-(3-(2-methylphenoxy)-phenoxy)-6-methoxy-2-methyl-pyrimidin-5-yl]-β-methoxyacrylate.

The double bond in formula I and II may be in E or Z-form. In this document the E and Z-forms are identified where meant specifically. In all other cases mixtures of the two isomers are intended. Dependent on the synthesis conditions used, the E- and Z-isomers are produced in different ratios from 100% E/0% Z to about 30% E/70% Z.

Where E an Z isomers are obtained during synthesis they may be separated by known techniques, such as crystallisation, chromatography or distillation.

Compounds of formula I are obtained by O-methylation of a compound of formula II

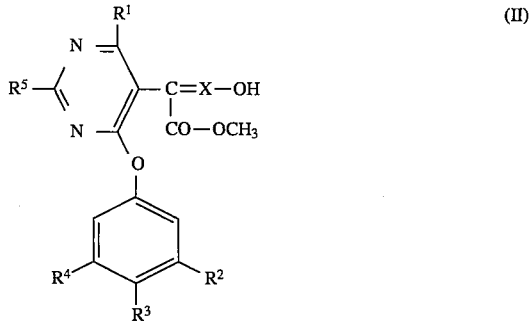

wherein $R^1$, $R^2$, $R^3$, $R^4$, $R^5$ and X are as defined above, resulting in compounds of subformula Ia

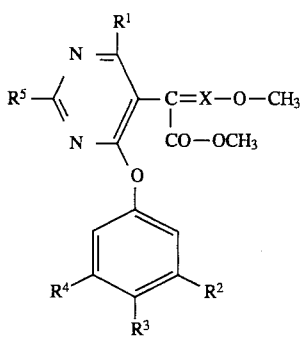

(Ia)

wherein X, R$^1$, R$^2$, R$^3$, R$^4$, R$^5$ and X are as defined above, and optionally converting the compounds of formula Ia into the compounds of subformula Ib

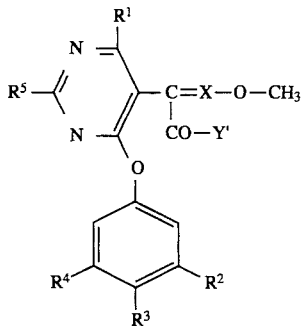

(Ib)

wherein R$^1$, R$^2$, R$^3$, R$^4$, R$^5$ and X are as defined above and Y' is NH$_2$, NHCH$_3$ or N(CH$_3$)$_2$, by an amidation reaction with NH$_3$, NH$_2$CH$_3$ or NH(CH$_3$)$_2$, respectively.

The O-methylation can be carried out in a manner known per se for the preparation of 3-methoxyacrylates employing conventional methylation agents. Examples of suitable methylation agents include methyl iodide and dimethylsulfate. The O-methylation is conveniently carried out in the presence of a base.

The reaction temperature will conveniently lie in the range of from 0° C. to the boiling point of the reaction mixture, e.g. at about ambient temperature. Inert solvents may be used where desired. Examples of suitable bases include alkaline metal hydrides such as sodium hydride, alkaline methyl alcoholates such as sodium methylate, alkaline metal carbonate or sodium hydrogen carbonate. Examples of suitable inert solvents include aromatic hydrocarbons such as benzene and toluene; ethers such as diethyl ether, tetrahydrofuran and 1,2-dimethoxyethane; polar solvents such as dimethylformamide, dimethyl sulfoxide, water, alcohols such as methanol; acetone or a mixture comprising two or more of them. The desired end-product is isolated and purified according to known techniques, for example by evaporation of solvent, chromatography and crystallisation. The compounds of formula I are basic in nature. They may form salts with sufficiently strong acids such as HCl and HBr.

The optional conversion of the compounds of subgroups Ia to subgroups Ib is a transamidation process which is carried out under the reaction conditions usually employed for this type of amidation reaction. Preferably, the ester compounds of formula Ia (Y is OCH$_3$) are treated with the amine component (ammonia, methylamine or dimethylamine). Advantageously, the reaction is carried out in an inert polar solvent like dimethylformamide, or in an excess of the amine. The reaction temperature is not critical, but will preferably be between 0° C. and +60° C., e.g. at room temperature.

The compounds of formula II wherein X is CH may be obtained by reaction of compounds of formula III

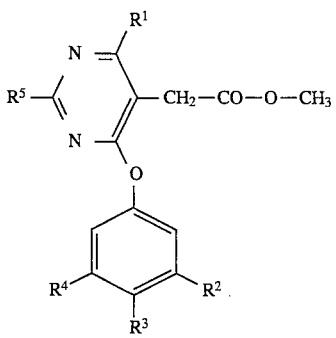

(III)

wherein R$^1$, R$^2$, R$^3$, R$^4$ and R$^5$ are as defined above with a formylating agent, e.g. N,N-diformylmethylamine, or methyl formate in the presence of a base.

This reaction is essentially a Claisen reaction and may be carried out under the conditions known for such reaction. The reaction (III–>II) may be carried out in an inert solvent. Examples of suitable solvents are as described for the O-methylation of the compounds of formula (II). Examples of suitable bases are such typically used for a Claisen reaction such as alkaline metal alcoholates, e.g. sodium methylate; alkaline metal hydrides, e.g. sodium hydride; and lithium amides or sodium amides, e.g. lithium diethylamide. The reaction temperature may vary within wide ranges, e.g. from 0° C. to the boiling point of the reaction mixture and is preferably at or near ambient temperature.

The compounds of formula II wherein X is N may be obtained by reacting a compound of formula III with an alkyl nitrite in the presence of a base, optionally in the presence of an inert solvent. In a variant of this process the compounds of formula II wherein X is N may also be obtained by reacting a compound of formula III with an alkyl nitrite in the presence of hydrochloric acid, optionally in an inert solvent. The reaction temperature will conveniently lie in the range of from –40° C. to +30° C. e.g. at about –20° C. to 0° C. Inert solvents may be used where desired. Examples of suitable bases include alkaline metal hydroxides such as sodium hydroxide, alkaline metal hydrides such as sodium hydride and alkaline metal alcoholates such as sodium methylate. Examples of suitable inert solvents include aromatic hydrocarbons such as benzene and toluene; ethers such as diethyl ether, tetrahydrofuran and 1,2-dimethoxyethane; polar solvents such as dimethylformamide, dimethyl sulfoxide, water, alcohols such as methanol; acetone or a mixture comprising two or more of them.

In a variant of the two-step process (III→II→I), the compounds of formula I may be obtained by a single-vessel reaction from compounds of formula III, without isolation and purification of the intermediate compounds of formula II.

The acetic acid esters of formula III may be obtained from compounds of formula IVa when R$_1$ is C$_{1-4}$alkoxy

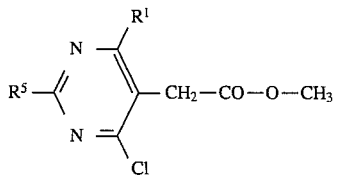

(IVa)

wherein R$^1$ is C$_{1-4}$alkoxy and R$^5$ is as defined above, by reacting it with a phenol of formula V

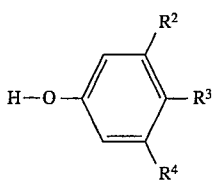

wherein $R^2$, $R^3$ and $R^4$ are as defined above in the presence of a base and an inert solvent. Suitable bases and solvents are as for (II→I), or from compounds of formula IVb when $R_1$ is -$NR_8R_9$

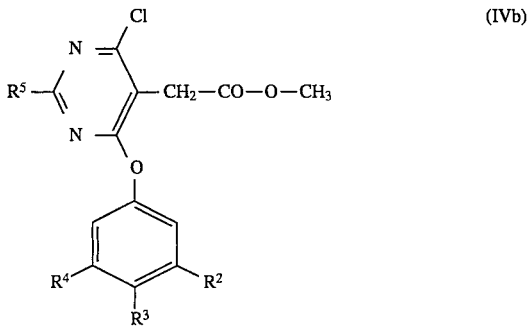

wherein $R^2$, $R^3$, $R^4$ and $R^5$ are as defined above, by reacting it with an amine $HNR_8R_9$, wherein $R_8$ and $R_9$ are as defined above.

The compounds of formula IVa may be obtained by reacting dichloropyrimidinyl acetic ester of formula VI

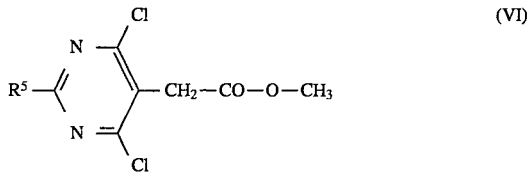

wherein $R^5$ is as defined above, with a compound of the formula VII $$H\text{-}R^1 \quad\quad (VII)$$

wherein $R^1$ is as defined above, in the presence of a base and an inert solvent.

The compounds of formula IVb may be obtained by reacting dichloropyrimidinyl acetic ester of formula VI with a phenol of formula V in the presence of a base and an inert solvent.

The reaction temperature is with advantage kept below +20° C. with cooling. Suitable bases are for example sodium methylate, for $R^1$ being methoxy, and tertiary amines, e.g. triethylamine, for $R^1$ being $NR^8R^9$.

The compounds of formula VI may be obtained by reacting a compound of formula VIII

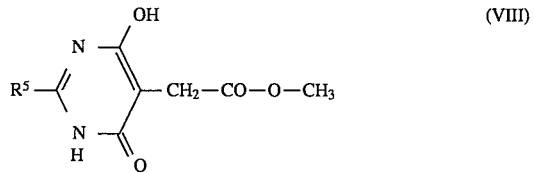

wherein $R^5$ is as defined above, with a chlorinating agent, preferably in the presence of a base.

The reaction is preferably carried out at elevated temperatures (up to +130° C.). Suitable chlorinating agents are $POCl_3$, $COCl_2$, $SOCl_2$ or $PCl_5$. Suitable bases are tertiary amines, such as N,N-diethylaniline.

The compounds of formula VIII may be obtained by reacting a compound of formula IX

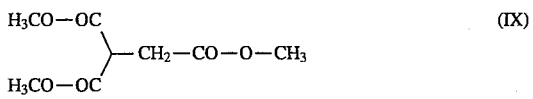

with formamidine or acetamidine in the presence of a base.

The reaction is preferably carried out with cooling at a temperature between −20° C. and +20° C. in an inert solvent. A suitable solvent is methanol. The suitable base is sodium methylate.

The intermediates of formulae II, III, IVa, IVb, VI and VIII have especially been developed for the synthesis of the compounds of formula I. They therefore also constitute a part of present invention.

Where derivatisation of the compounds of formula I into other compounds of formula I is desired, e.g. by transforming certain radicals into other radicals, which also are within the definition of formula I, such derivatisation may be effected by chemical methods known per se, e.g. acetalisation, amidation, transesterification and the like.

The starting materials of formulae V, VII and IX are known, or can be obtained according to methods known per se, or by methods analogous to the methods used for known compounds.

The intermediates of formula III wherein $R^2$ is -$C(CH_3)$=N-O-$R^6$ or

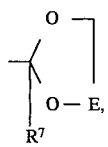

may suitably be prepared from the corresponding carbonyl compound of formula X

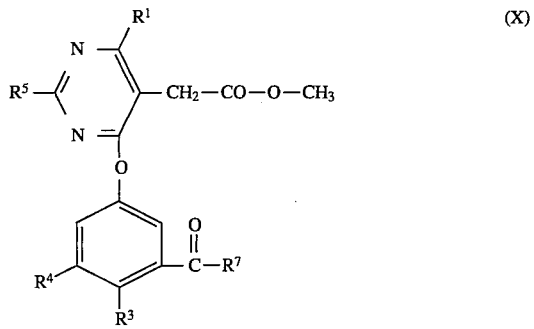

wherein $R^1$, $R^3$, $R^4$, $R^5$ and $R^7$ are as defined above, with a suitable acetalising agent of formula XI

wherein E is as defined above, or with an oxime forming agent of formula XII $$H_2N\text{-}O\text{-}R^6 \quad\quad (XII)$$

wherein $R^6$ is as defined above.

The compounds of formula X have especially been prepared for the synthesis of the compounds of formula I. They are thus a part of present invention.

The compounds of formula I are effective against phytopathogens.

Their advantageous fungicidal activity is established by in vivo tests with test concentrations from 0.5 to 500 mg a.i./l against *Uromyces appendiculatus* on pole beans, against *Puccinia triticina* on wheat, against *Sphaerotheca fuliginea* on cucumber, against *Erysiphe graminis* on wheat and barley, against *Podosphaera leucotricha* on apple, against *Uncinula necator* on grape vine, against *Leptosphaeria nodorum* on wheat, against *Cochliobolus sativus* and *Pyrenophora graminea* on barley, against *Venturia inaequalis* on apple, against *Phytophthora infestans* on tomato and against *Plasmopara viticola* on grape vine.

Many of the compounds of formula I have an excellent plant tolerance and a systemic action. The compounds of the invention are therefore indicated for treatment of plant, seeds and soil to combat phytopathogenic fungi, e.g. Basidiomycetes of the order Uredinales (rusts) such as Puccinia spp, Hemileia spp, Uromyces spp; and Ascomycetes of the order Erysiphales (powdery mildew) such as Erysiphe ssp, Podosphaera spp, Uncinula spp, Sphaerotheca spp; as well as Cochliobolus; Pyrenophora spp; Venturia spp; Mycosphaerella spp; Leptosphaeria; Deuteromycetes such as Pyricularia, Pellicularia (Corticium), Botrytis; and Oomycetes such as Phytophthora spp, Plasmopara spp.

The compounds of formula I are particularly effective against powdery mildew and rust, Pyrenophora and Leptosphaeria fungi, in particular against pathogens of monocotyledonous plants such as cereals, including wheat and barley.

The amount of compound of the invention to be applied, will depend on various factors such as the compound employed, the subject of the treatment (plant, soil, seed), the type of treatment (e.g. spraying, dusting, seed dressing), the purpose of the treatment (prophylactic or therapeutic), the type of fungi to be treated and the application time.

In general, satisfactory results are obtained, if the compounds of the invention are applied in an amount of from about 0.01 to 1.0, preferably about 0.05 to 0.5 kg/ha, in the case of a plant or soil treatment; e.g. 0.05 to 0.5 kg of active ingredient (a.i.) per ha in field crops such as cereals, or concentrations of 5 to 50 g of a.i. per hl in crops such as fruits, vineyards and vegetables (at an application volume of from 300 to 1000 l/ha—depending on the size or leaf volume of the crop—which is equivalent to an application rate of approximately 15 to 500 g/ha). The treatment can, if desired, be repeated, e.g. at intervals of 8 to 30 days.

Where the compounds of the invention are used for seed treatment, satisfactory results are in general obtained, if the compounds are used in an amount of from about 0.05 to 0.5, preferably about 0.1 to 0.3 g/kg seeds.

The term soil as used herein is intended to embrace any conventional growing medium, whether natural or artificial.

The compounds of the invention may be used in a great number of crops, such as soybean, coffee, ornamentals (i.a. pelargonium, roses), vegetables (e.g. peas, cucumber, celery, tomato and bean plants), sugarbeet, sugarcane, cotton, flax, maize (com), vineyards, pomes and stone fruits (e.g. apple, pears, prunes) and in cereals (e.g. wheat, oats, barley, rice).

The invention also provides fungicidal compositions, comprising as a fungicide a compound of formula I in association with an agriculturally acceptable diluent (hereinafter diluent). They are obtained in conventional manner, e.g. by mixing a compound of the invention with a diluent and optionally additional ingredients, such as surfactants.

The term diluent as used herein means liquid or solid agriculturally acceptable material, which may be added to the active agent to bring it into an easier or better applicable form, resp. to dilute the active agent to a usable or desirable strength of activity. Examples of such diluents are talc, kaolin, diatomaceous earth, xylene or water.

Especially formulations used in spray form, such as water dispersible concentrates or wettable powders, may contain surfactants such as wetting and dispersing agents, e.g. the condensation product of formaldehyde with naphthalene sulphonate, an alkylarylsulphonate, a lignin sulphonate, a fatty alkyl sulphate, an ethoxylated alkylphenol and an ethoxylated fatty alcohol.

In general, the formulations include from 1% to 90% by weight of active agent, from 0% to 20% agriculturally acceptable surfactant and from 10% to 99% diluent(s). Concentrated forms of composition, e.g. emulsion concentrates, contain in general from about 5% to 70%, preferably from between 10% and 50% by weight of active agent. Application forms of formulation contain in general from 1 ppm to 5000 ppm of a compound of the invention as active agent. Typical spray-suspensions may, for example, contain from 10 ppm to 1000 ppm, preferably from 50 ppm to 500 ppm, e.g. 100 ppm or 500 ppm of active agent. In addition to the usual diluents and surfactants, the compositions of the invention may comprise further additives with special purposes, e.g. stabilisers, desactivators (for solid formulations or carriers with an active surface), agents for improving the adhesion to plants, corrosion inhibitors, anti-foaming agents and colorants. Moreover, further fungicides with similar or complementary fungicidal activity, e.g. sulphur, chlorothalonil, euparen; a guanidine fungicide such as guazatine; dithiocarbamates such as mancozeb, maneb, zineb, propineb; trichloromethane sulphenylphthalimides and analogues such as captan, captafol and folpet; benzimidazoles such as carbendazim, benomyl; azoles such as cyproconazole, flusilazole, flutriafol, hexaconazole, propiconazole, tebuconazole, epoxiconazole, prochloraz; morpholines such as fenpropimorph, fenpropidine, or other beneficially-acting materials, such as cymoxanil, oxadixyl, metalaxyl, or insecticides or acaricides may be present in the formulations.

Examples of plant fungicide formulations are as follows:

a. Wettable Powder Formulation

10 Parts of a compound of formula I are mixed and milled with 4 parts of synthetic fine silica, 3 parts of sodium lauryl sulphate, 7 parts of sodium lignin sulphonate and 66 parts of finely divided kaolin and 10 parts of diatomaceous earth until the mean particle size is about 5 micron. The resulting wettable powder is diluted with water before use to a spray liquor which may be applied by foliar spray as well as by root drench application.

b. Granules

Onto 94.5 parts by weight of quartz sand in a tumbler mixer are sprayed 0.5 parts by weight of a binder (non-ionic tenside) and the whole thoroughly mixed. 5 parts by weight of a compound of formula I of this invention are then added and thorough mixing continued to obtain a granulate formulation with a particle size in the range of from 0.3 to 0.7 mm (where required, the granules may be dried by the addition of 1% to 5 % by weight of talcum). The granules may be applied by incorporation into the soil adjacent to the plants to be treated.

c. Emulsion Concentrate

10 Pans by weight of a compound of formula I are mixed with 10 parts by weight of an emulsifier and 80 pans by weight of xylene. The thus obtained concentrate is diluted with water to form an emulsion of the desired concentration, prior to application.

d. Seed Dressing

45 Parts of a compound of formula I are mixed with 1.5 parts of diamyl phenoldecaglycolether ethylene oxide adduct, 2 parts of spindle oil, 51 parts of fine talcum and 0.5 parts of colorant rhodanin B. The mixture is ground in a contraplex mill at 10,000 rpm until an average particle size of less than 20 microns is obtained. The resulting dry powder has good adherence and may be applied to seeds, e.g. by mixing for 2 to 5 minutes in a slowly turning vessel.

The following examples further illustrate the present invention. All temperatures are in centigrade.

EXAMPLE 1

Methyl α-[4-(3-methylphenoxy)-6-methoxy-pyrimidin-5-yl]-β-methoxyacrylate

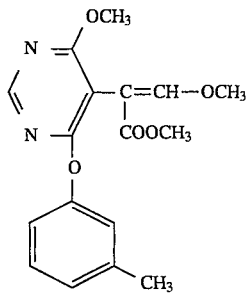

a) Methyl 4,6-dihydroxy-pyrimidin-5-yl-acetate

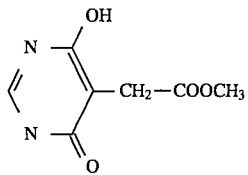

Trimethyl ethane-1,1,2-tricarboxylate (600 g, 3.0 mol) and formamidine acetate (312 g, 3.0 mol) are added sequentially to a vigourously stirred solution of sodium methylate (324 g, 6.0 mol) in methanol (1800 ml) at 0° C. The reaction mixture is stirred for 12 hours, diluted with t-butylmethyl ether (300 ml) and filtered with suction. The mixture of salts obtained is suspended in water (1000 ml) and acidified with concentrated hydrochloric acid (600 ml). Filtration and drying gives the methyl 4,6-dihydroxy-pyrimidin- 5-yl-acetate or the tautomeric forms thereof as a white solid (420 g), m.p. >200° C.

b) Methyl 4,6-dichloro-pyrimidin-5-yl-acetate

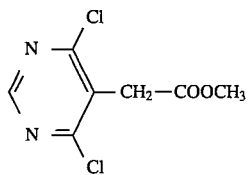

A suspension of methyl 4,6-dihydroxy-pyrimidin-5-yl-acetate (204 g, 1.1 mol) in phosphorus oxychloride (303 ml, 3.3 mol) and N,N-diethylaniline (352 ml, 2.2 mol) is heated to +130° C. for 3 hours. The dark homogeneous mixture is hydrolyzed by adding crushed ice, the temperature being kept below +30° C. Extraction with diethylether, drying ($MgSO_4$) and crystallization from hexane gives the methyl 4,6-dichloro-pyrimidin- 5-yl-acetate as cream colored crystals (195 g), m.p. 65°–67° C.

c) Methyl 4-chloro-6-methoxy-pyrimidin-5-yl-acetate

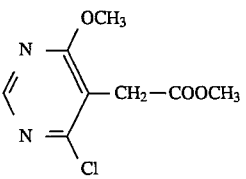

Sodium methylate in methanol (112 ml of a 5.4 molar solution) is added at room temperature to a solution of methyl 4,6-dichloro-pyrimidin-5-yl-acetate (120 g, 0.54 mol) in 1,2-dimethoxyethane (200 ml) with cooling. The reaction mixture is stirred for 30 minutes and poured on crushed ice. The precipitated crystals are filtered and dried to give the methyl 4-chloro-6-methoxy-pyrimidin-5-yl-acetate (106 g), m.p. 64° C.

d) Methyl 4-(3-methylphenoxy)-6-methoxy-pyrimidin-5-yl-acetate

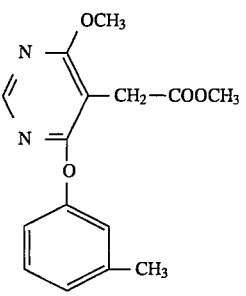

A mixture of methyl 4-chloro-6-methoxy-pyrimidin-5-yl-acetate (21.7 g, 100 mmol), m-cresol (10.8 g, 100mmol), potassium carbonate (20.7 g, 150 mmol) and a catalytic amount of 18-crown-6 in dimethylformamide (50 ml) is heated to +120° C. for 1 hour. Addition of crushed ice, extraction with ether and drying gives the methyl 4-(3-methylphenoxy)-6-methoxy-pyrimidin-5-yl-acetate as an oil.

$^1$H-NMR ($CDCl_3$): 8.36 (s, 1H); 7.32–6.88 (m, 4H); 4.02 (s, 3H); 3.72 (s, 2H); 3.70 (s, 3H); 2.37 (s, 3H) ppm.

e) Methyl 4-(3-methylphenoxy)-6-methoxy-pyrimidin-5-yl-acetate (12.1 g, 42 mmol)is dissolved in a mixture of 1,2-dimethoxyethane (120 ml) and methyl formate (50 ml). Sodium hydride (2.5 g, 80% in oil, 84 mmol) is added in one portion, the temperature being kept at room temperature. After 5 hours dimethylsulfate (6.6 ml, 70 mmol) is added with cooling. After an additional 5 hours the reaction mixture is diluted with ether and washed with brine. Drying and chromatography on silicagel (eluant: hexane/ethyl acetate 1:1) gives the E-isomer of methyl α-[4-(3-methylphenoxy)- 6-methoxy-pyrimidin-5-yl)-β-methoxyacrylate as a crystalline solid, m.p. 107° C.

EXAMPLE 2

Methyl α-[4-(3-tert.butylphenoxy)-6-dimethylamino-pyrimidin-5-yl]-β-methoxyacrylate

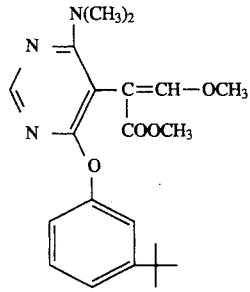

a) Methyl 4-chloro-6-dimethylamino-pyrimidin-5-yl-acetate

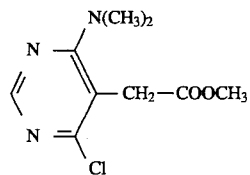

Dimethylamine (50 ml of a 40% aqueous solution) is added dropwise to a solution of methyl 4,6-dichloropyrimidin-5-yl-acetate (80 g, 0.36 mol) in 1,2-dimethoxyethane (300 ml) and triethylamine (56 ml, 0.4 mol) at room temperature with cooling. After stirring for 1 hour the mixture is diluted with water and the product extracted with diethyl ether. Drying (MgSO$_4$), evaporation of the solvent and distillation gives the methyl 4-chloro-6-dimethylamino-pyrimidin-5-yl-acetate as a colorless solid (74 g), b.p. 135°–138° C./1.5 torr, m.p. 30°–32° C.

b) Methyl 4-(3-tert.butylphenoxy)-6-dimethylamino-pyrimidin-5-yl-acetate

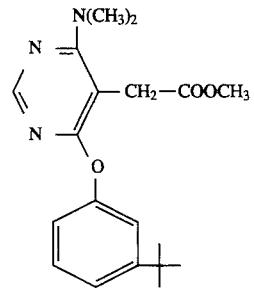

A mixture of methyl 4-chloro-6-dimethylamino-pyrimidin-5-yl-acetate (22.9 g, 100 mmol), 3-tert.butylphenol (15.0 g, 100 mmol), potassium carbonate (20.7 g, 150 mmol) and a catalytic amount of 18-crown-6 is heated in dimethylformamide (50 ml) at 130° C. for 6 hours. The reaction mixture is diluted with diethyl ether, washed with 2n NaOH and brine, dried (MgSO$_4$) and evaporated to give methyl 4-(3-tert.butylphenoxy)- 6-dimethylamino-pyrimidin-5-yl-acetate as a yellow oil (30 g).

$^1$H-NMR (CDCl$_3$): 8.29 (s, 1H); 7.35–6.88 (m, 4H); 3.76 (s, 2H); 3,74 (s, 3H); 3.07 (s, 6H); 1.32 (s, 9H) ppm.

c) Methyl 4-(3-tert.butylphenoxy)-6-dimethylamino-pyrimidin-5-yl-acetate (10.0 g, 29 mmol) is dissolved in a mixture of 1,2-dimethoxyethane (60 ml) and methyl formate (20 ml). Sodium hydride (1.7 g, 80% in oil, 58 mmol) is added in one portion, the temperature being kept at room temperature. After 5 hours the reaction mixture is carefully acidified with hydrochloric acid. After stirring for 1 hour at +5° C. the mixture is neutralized with solid sodium bicarbonat. The intermediate product is extracted with ether and worked up in the usual way. The resulting oil is stirred in dimethylformamide (20 ml) and dimethyl sulfate (4.7 ml, 50 mmol) for 2 hours at room temperature. Dilution with ether washing with brine and chromatography on silicagel (eluant:hexane/ethyl acetate 1:1) gives the methyl α-[4-(3-tert.butylphenoxy)-6-dimethylamino-pyrimidin- 5-yl]-β-methoxyacrylate as a single isomer (5.5 g).

$^1$H-NMR (CDCl$_3$): 8.24 (s, 1H); 7.49 (s, 1H); 7.31–6.80 (m, 4H); 3.87 (s, 3H); 3.73 (s, 3H); 3.08 (s, 6H); 1.30 (s, 9H) ppm.

EXAMPLE 3

Methyl α-[4-(3-(2-methyldioxolan-2-yl)-phenoxy)-6-methoxy-pyrimidin-5-yl]-β-methoxyacrylate

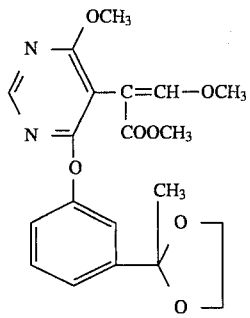

a) Methyl 4-(3-acetylphenoxy)-6-methoxy-pyrimidin-5-yl-acetate

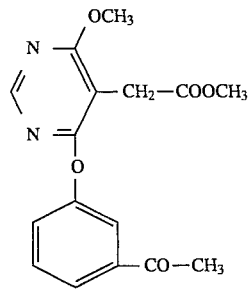

A mixture of methyl 4-chloro-6-methoxy-pyrimidin-5-yl-acetate (21.7 g, 100 mmol), 3-hydroxyacetophenone (13.6 g, 100 mmol), potassium carbonate (20.7 g, 150 mmol) and a catalytic amount of 18-crown-6 in dimethylformamide (50 ml) is heated to +120° C. for 1 hour. Addition of crushed ice, filtration and drying gives the methyl 4-(3-acetylphenoxy)-6-methoxy-pyrimidin-5-yl-acetate (28.5 g) having a m.p. of 65°–67° C.

b) Methyl 4-[3-(2-methyl-dioxolan-2-yl)-phenoxy]-6-methoxy-pyrimidin-5-yl-acetate

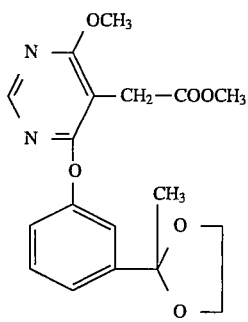

A mixture of methyl 4-(3-acetylphenoxy)-6-methoxy-pyrimidin-5-yl-acetate (15.0 g, 47 mmol), ethylene glycol (7.9 ml, 140 mmol) and p-toluene sulfonic acid is refluxed, removing the water azeotropically. After two hours the organic phase is washed with saturated sodium carbonate solution, dried (MgSO₄) and evaporated to give the methyl 4-[3-(2-methyldioxolan-2-yl)-phenoxy]-6-methoxy-pyrimidin-5-yl-acetate as a yellow oil (16.2 g).

¹H-NMR (CDCl₃): 8.36 (s, 1H); 7.40–7.02 (m, 4H); 4.08–4.00 (m, 4H); 4.02 (s, 3H); 3.82–3.74 (m, 4H); 3.74 (s, 2H); 3.72 (s, 3H); 1.67 (s, 3H) ppm.

c) Methyl 4-[3-(2-methyldioxolan-2-yl)-phenoxy]-6-methoxy-pyrimidin-5-yl-acetate (15.0 g, 42 mmol) is dissolved in a mixture of 1,2-dimethoxyethane (120 ml) and methyl formate. Sodium hydride (2.5 g, 80% in oil, 84 mmol) is added in one portion, the temperature being kept at room temperature. After 5 hours dimethylsulfate (6.6 ml, 70 mmol) is added with cooling. After an additional 5 hours the reaction mixture is diluted with ether and washed with brine. Drying and chromatography on silicagel (eluant: hexane/ethyl acetate 1:1) gives the E-isomer of methyl α[4-(3-(2-methyldioxolan-2-yl)- 6-methoxy-5-pyrimidin-5-yl]-β-methoxyacrylate as a crystalline solid (5.5. g), m.p. 91°–93° C. and the Z-isomer (4.2 g) as an oil.

¹H-NMR (CDCl₃): 8.32 (s, 1H); 7.40–6.96 (m, 4H); 6.73 (s, 1H); 4.07–3.99 (m, 2H); 4.00 (s, 3H); 3.96 (s, 3H); 3.82–3.74 (m, 4H); 3.70 (s, 3H); 1.65 (s, 3H) ppm

EXAMPLE 4

Methyl α-[4-(3-(2-cyanophenoxymethyl)-phenoxy)-6-methoxy-pyrimidin-5-yl]-β-methoxyacrylate

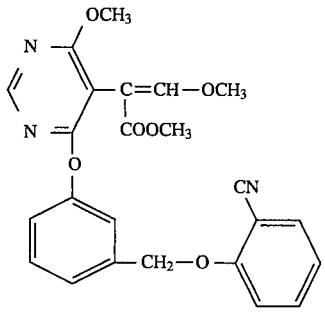

a) Methyl α-[4-(3-bromomethylphenoxy)-6-methoxy-pyrimidin-5-yl]-β-methoxyacrylate

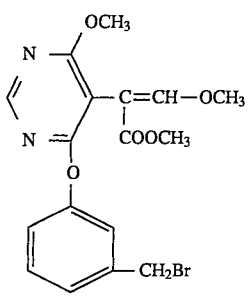

Methyl α-[4-(3-methylphenoxy)-6-methoxy-pyrimidin-5-yl]-[3-methoxy acrylate (2.7, 8.4 mmol), N-bromosuccinimide (1.6 g, 6 mmol) and a catalytic amount of AIBN are refluxed in CCl₄ for 90 minutes. Filtration of the succinimide and evaporation of the solvent gives the methyl α-[4-(3-bromomethylphenoxy)-6-methoxy-pyrimidin-5-yl]-β-methoxyacrylate as a colorless oil.

¹H-NMR (CDCl₃): 8.38 (s, 1H); 7.60 (s, 1H); 7.39–7.00 (m, 4H); 4.48 (s, 2H); 4.00 (s, 3H); 3.85 (s, 3H); 3.72 (s, 3H) ppm b) Methyl α-[4-(3-bromomethylphenoxy)-6-methoxy-5-pyrimidinyl]-β-methoxyacrylate (3.2 g, 7.8 mmol), o-hydroxybenzonitril (0.93 g, 7.8 mmol) and potassium carbonate (2.1 g, 15 mmol) are stirred in dimethylformamide (20 ml) for 4 hours at room temperature. Dilution with ether, washing with brine, drying (MgSO₄) and chromatography on silicagel (eluent: hexane/ethyl acetate 1:1) gives methyl α-[4-(3-( 2-cyanophenoxymethyl)-phenoxy)-6-methoxy-pyrimidin-5-yl]-β-methoxyacrylate as a colorless solid (3.0 g), m.p. 132°–135° C.

¹H-NMR (CDCl₃): 8.35 (s, 1H); 7.58 (s, 1H); 7.55–6.93 (m, 8H); 5.19 (s, 2H); 3.97 (s, 3H); 3.85 (s, 3H); 3.70 (s, 3H) ppm.

EXAMPLE 5

Methyl α-[4-(3-isopropylphenoxy)-6-methoxy-2-methyl-pyrimidin;5-yl]-β-methoxyacralate

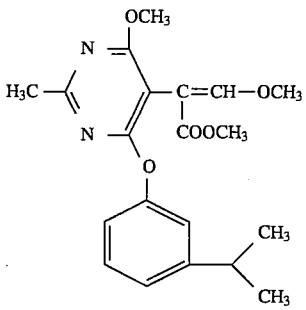

(II)

a) Methyl 4,6-dihydroxy-2-methylpyrimidin-5-yl-acetate

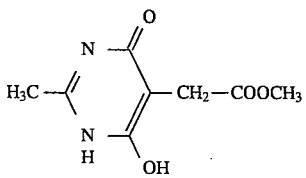

Trimethyl ethane-1,1,2-tricarboxylate (204 g, 1 mol) and acetamidine hydrochloride (95 g, mol) are added to a solution of sodium methylate (108 g, 2 mol) in methanol (600 ml) with stirring. The mixture is stirred for 16 hours at room temperature. Acidification with concentrated hydrochloric acid, filtration, washing with cold water and drying gives the methyl 4,6-dihydroxy-2-methyl-pyrimidin-5-yl-acetate (or tautomeric forms thereof) as a colorless solid (210 g), m.p.>200° C.

$^1$H-NMR (d$^6$-DMSO):11.95 (s, br, 2H); 3.54 (s, 3H); 3.20 (s, 2H); 2.23 (s, 3H).

b) Methyl 4,6-dichloro-2-methyl-pyrimidin-5-yl-acetate

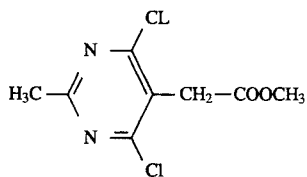

A suspension of methyl 4,6-dihydroxy-2-methyl-pyrimidin-5-yl-acetate (175 g, 0.88 mol) in phosphorous oxychloride (230 ml, 2.6 mol) and N,N-diethylaniline (280 ml, 1.75 mol) is heated at 130° C. for 1 hour. The mixture is poured onto crushed ice/water. The crystalline product is filtered and washed with water. Drying gives the methyl 4,6-dichloro-2-methyl-pyrimidin-5-yl-acetate in form of grey crystals (180 g), m.p. 70°–72° C.

c) Methyl 4-chloro-6-methoxy-2-methyl-pyrimidin-5-yl-acetate

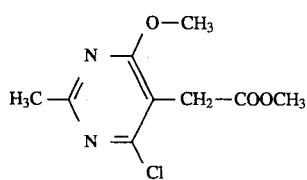

Sodium methylate in methanol (33 ml of a 5.4 molar solution) is added at room temperature to a solution of methyl 4,6-dichloro-2-methyl-pyrimidin-5-yl-acetate (35.5 g, 0.15 mol) in 1,2-dimethoxyethane (60 ml). After stirring for 30 minutes the mixture is diluted with diethyl ether and washed with water. Drying and distillation gives the methyl-chloro-6-methoxy-2-methyl-pyrimidin-5-yl-acetate as a colorless oil (30 g), b.p. 108°–110° C./0.5 torr.

d) Methyl 4-(3-isopropylphenoxy)-6-methoxy-2-methyl-pyrimidin-5-yl-acetate

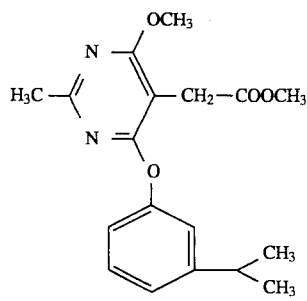

4-Chloro-6-methoxy-2-methyl-pyrimidin-5-yl-acetate (23 g, 0.1 mol), 3-isopropylphenol (13.6 g, 0.1 mol) and potassium carbonate (20.7 g, 0.15 mol) are heated in dimethylformamide (50 ml) for 2 hours at 130° C. Dilution with diethylether, washing with water, drying and chromatography on silicagel (eluant ethyl acetate/hexane 1:3) gives the methyl H-(3-isopropylphenoxy)-6-methoxy-2-methyl-pyrimidin-5-yl-acetate as a colorless solid (21.5 g). Alternatively, the coupling may be conducted at 120° C. with 10 mol % CuI as catalyst to give a similar yield of the product.

$^1$H-NMR (CDCl$_3$): 7.28–6.82 (m, 4H); 4.02 (s, 3H); 3.72 (s, 2H); 3.70 (s, 3H); 2.88 (dq, 1H); 2.32 (s, 3H); 1.22 (d, 6H).

e) A solution of methyl 4-(3-isopropylphenoxy)-6-methoxy-2-methyl-pyrimidin-5-yl-acetate (8.6 g, 26 mol) in 1,2-dimethoxyethane (20 ml) and N,N-diformylmethylamine (8 ml) is added at 5° C. to a suspension of NaH (1.6 g, 80% in oil, 52 mol) in DMF (30 ml). The mixture is stirred for 4 hours at room temperature. Dimethylsulfate (3.7 ml, 39 tool) is added at 0° C and stirring is continued for 3 hours. Dilution with ether, washing with brine and chromatography on silicagel (eluent hexane/ethyl acetate 3:1) gives methyl α-[4-(3-isopropylphenoxy )-6-methoxy-2-methyl-pyrimidin-5-yl]-β-methoxyacrylate as a colorless oil (7.2 g, 74%).

$^1$H-NMR (CDCl$_3$): reported in Table 2, compound 2.03.

EXAMPLE 6

Methyl 2-[4-(3-(1-(3-chlorobenzyloximino)-ethyl)-phenoxy)-6-dimethylamino-pyrimidin-5-yl-2-methoximino-acetate

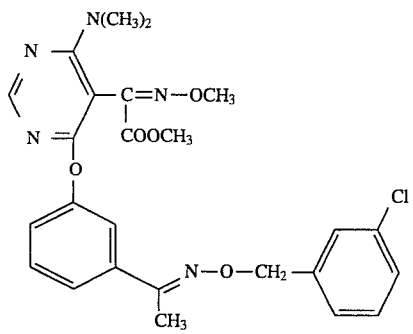

a) Methyl 4-(3-acetylphenoxy)-6-dimethylamino-pyrimidin-5-yl-acetate

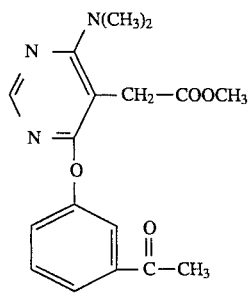

A mixture of methyl 4,6-dichloropyrimidin-5-yl-acetate (221 g, 1 mol), 3-hydroxyacetophenone (136 g, 1 mol) and K$_2$CO$_3$ (207 g, 1.5 mol) in DMF (150 mol) is stirred at 100° C. for 90 minutes. The dark mixture is cooled to 0° C. and dimethylamine (450 ml of a 40% aqeous solution) is added. Stirring is continued at room temperature for hours. Dilution with water and extraction with ether gives methyl 4-(3-acetylphenoxy)- 6-dimethylamino-pyrimidin-5-yl-acetate as a brownish oil (purity>95%).

b) Methyl 4-[3-(1-hydroximinoethyl)-phenoxy]-6-dimethylamino-pyrimidin-5-yl-acetate

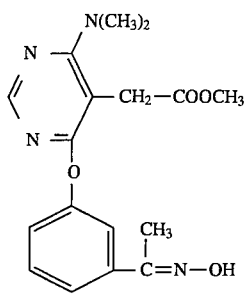

The methyl 4-(3-acetylphenoxy)-6-dimethylamino-pyrimidin-5-yl-acetate obtained is dissolved in 500 ml methanol, and hydroxylamine hydrochloride (76 g, 1.1 mol) and sodium acetate (107 g, 1.3 mol) are added at 0° C. After stirring for 2 hours at room temperature the product is crystallized by adding water. Filtering and drying gives methyl -[3-(1-hydroximinoethyl)-phenoxy]-6-dimethylamino-pyrimidin-5-yl-acetate in form of yellowish crystals (292 g) having a m.p. of 113°–115° C.

c) Methyl 4-[3-(1-(3-chlorobenzyloximino)-ethyl)-phenoxy]- 6-dimethylamino-pyrimidin-5-yl-acetate

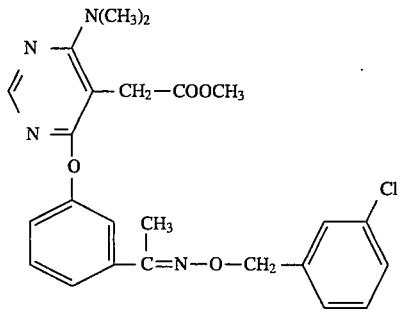

A mixture of methyl 4-[3-( 1 -hydroximinoethyl)-ethyl)-phenoxy]-dimethylamino-pyrimidin- 5-yl-acetate (34.4 g, 0.1 mol), 3-chlorobenzylchloride (16.1 g, 0.1 mol) and $K_2CO_3$ (20.7 g, 0.15 mol) in DMF (30 ml) are heated with stirring to 110° C. for 3 hours. Dilution with ether and washing with water gives methyl 4-[3-(1-(3-chlorobenzyloximino)-ethyl)-phenoxy]- 6-dimethylamino-pyrimidin-5-yl-acetate (44 g) as a yellowish colored oil.

d) Methyl 2-[4-(3-(1-(3-chlorobenzyloximino)-ethyl-phenoxy)-6-dimethylamino-pyrimidin- 5-yl]-2-hydroximino-acetate

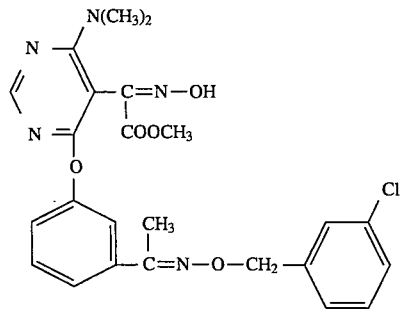

A solution of methyl 4-[3-( 1-(3-chlorobenzyloximino)-ethyl)-phenoxy]- 6-dimethylamino-pyrimidin-6-yl-acetate (44 g, 0.094 mol) in 1,2-dimethoxyethane (50 ml) and t-butylnitrite (20 ml) is added slowly to a solution of potassium tertiary butylate (16 g, 0.14 mol) in 1,2-dimethoxyethane (100 ml) at −20° C. After stirring for 1 hour at room temperature the reaction is quenched by adding a saturated solution of $NH_4Cl$ in water. Stirring is continued for 2 hours. Extraction and chromatography on silicagel (eluent: hexane/ethyl acetate 2:1) gives the E-form of methyl 2-[4-(3-(1-(3-chlorobenzyloximino)-ethyl)-phenoxy)-6-dimethylamino-pyrimidin-5-yl]-2-hydroximino-acetate as a colorless oil (33 g, 71%).

e) To as suspension of NaiI (2.4 g, 80%, 80 mol) in dry DMF is added a solution of methyl 2-[4-(3-( 1 -(3-chlorobenzyloximino)-ethyl)-phenoxy )-6-dimethylamino-pyrimidin- 5-yl]-2-hydroximino-acetate (33 g, 66 mmol) and dimethylsulfate (7.6 m, 80 mmol) in DMF at 0° C. The mixture is stirred for 4 hours. Dilution with ether, washing with water and chromatography on silicagel (eluent: hexane, ethyl acetate 3:1) gives methyl 2-[4-(3-(1-( 3-chlorobenzyloximino)-ethyl)-phenoxy)-6-dimethylamino-pyrimidin-5-yl]-2-methoximino-acetate as a colorless oil (24 g, 71%).

$^1$H-NMR (CDCl$_3$) reported in Table 3, compound 3.03.

EXAMPLE 7

N-methyl 2-[4-(3-isopropylphenoxy)-6-dimethylamino-2-methyl-pyrimidin-5-yl]- 2-methoximino-acetamide

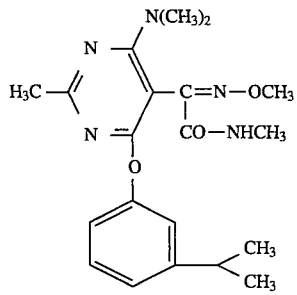

a) Methyl 4-(3-isopropylphenoxy)-6-dimethylamino-2-methyl-pyrimidin-5-yl-acetate

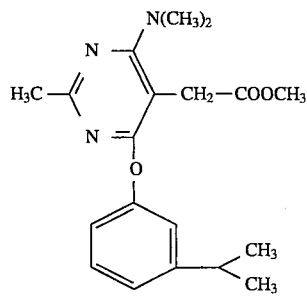

Methyl 4,6-dichloro-2-methyl-pyrimidin-5-yl-acetate (23.5 g, 0.1 mol), 3-isopropylphenol (13.6 g, 0.1 mol) and potassium carbonate (20.7 g, 0.15 mol) are heated in dimethylformamide (30 ml) at 100° C. for 45 minutes. The mixture is cooled and an aqueous solution of dimethylamine (50 ml of a 40% solution) is added. Stirring is continued for 16 hours at room temperature. Addition of water, filtering and drying gives the methyl 1-dimethylamino-2-methyl-pyrimidin-5-yl-acetate as a brownish solid (28 g).

$^1$H-NMR (CDCl$_3$): 7.28–6.82 (m, 4H); 3.84 (s, 3H); 3.78 (s, 2H); 3.02 (s, 6H); 2.89 (dq, 1H); 2.37 (s, 3H); 1.23 (d, 6H).

b) Methyl 2-[4-(3-isopropylphenoxy)-6-dimethylamino-2-methyl-pyrimidin-5-yl]- 2-hydroximino-acetate

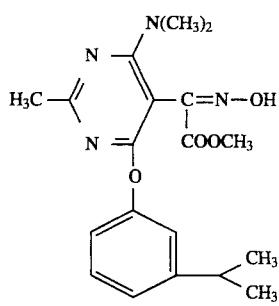

A solution of methyl 4-(3-isopropylphenoxy)-6-dimethylamino- 2-methyl-pyrimidin- 5-yl-acetate (28 g, 0.08 mol) in t-butylnitrite (40 ml) and 1,2-dimethoxyethane (40 ml) is added at −30° C. to a solution of potassium tert. butylate (14 g, 0.12 mol) in 1,2-dimethoxyethane (50 ml). The reaction mixture is allowed to warm to 0° C. and is the quenched with a solution of ammonium chloride. After stirring for 2 hours at room temperature the product is extracted with diethylether. Drying (MgSO$_4$) and evaporation of the solvent gives crude methyl 2-[4-(3 -isopropylphenoxy)-6-dimethylamino-2-methyl-pyrimidin-5-yl-]- 2-hydroximino-acetate (30 g).

c) Methyl 2-[4-(3-isopropylphenoxy)-6-dimethylamino-2-methyl-pyrimidin-5-yl]- 2-methoximino-acetate

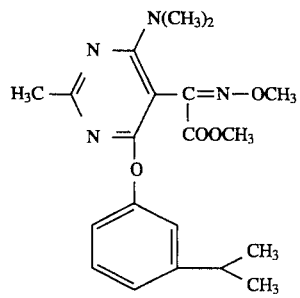

Methyl 2-[4-(3-isopropylphenoxy)-6-dimethylamino-2-methyl-pyrimidin-5-yl]- 2-hydroximino-acetate (30 g, 0.08 mol) is dissolved in a mixture of toluene (100 ml) and 1,2-dimethoxyethane (50 ml). Dimethylsulfate (8.6 ml, 0.09 mol) and sodium hydride (2.7 g of a 80% suspension in oil, 0.09 mol) are added sequentially at −10° C. The mixture is allowed to warm to room temperature and is stirred for 4 hours at this temperature. Dilution with ether, washing with water, drying and chromatography on silicagel (eluent ethyl acetate/hexane 1:3) gives methyl 2-[4-(3-isopropylphenoxy)-6-dimethylamino- 2-methyl-pyrimidin-5-yl]-2-methoximino-acetate as a colorless oil (16.2 g).

$^1$H-NMR (CDCl$_3$): 7.28–6.82 (m, 4H); 4.07 (s, 3H); 3.83 (s, 3H); 3.02 (s, 6H); 2.89 (dq, 1H); 2.37 (s, 3H); 1.23 (d, 6H).

d) A solution of methyl 2-[4-(3-isopropylphenoxy)-6-dimethylamino-2-methyl-pyrimidin- 5-yl]-2-methoximino-acetate (6.0 g, 15.5 mol) and methylamine (10 ml of an aqueous solution) in DMF (80 ml) is stirred for 48 hours at room temperature. The product is crystallized by adding water. Filtration and drying gives N-methyl 2-[4-( 3-isopropylphenoxy)-6-dimethylamino-2-methyl-pyrimidin-5 -yl]-2-methoximinoacetamide in form of colorless crystals, having a m.p. of 128°–129° C. (4.7 g, 78%).

TABLE 1

Compounds of formula I ($R^5$ = H; X = CH; Y = OCH$_3$)

| Comp. No. | $R^1$ | $R^2$ | $R^3$ | $R^4$ | Isomer | physical data $^1$H—NMR or/and m.p. |
|---|---|---|---|---|---|---|
| 1.01 | OCH$_3$ | C$_3$H$_7$-i | H | H | E | 78–80° C. |
| 1.02 | OCH$_3$ | C$_3$H$_7$-i | H | H | Z | 97–98° C. |
| 1.03 | OCH$_3$ | CF$_3$ | H | H | E | 109–110° C. |
| 1.04 | N(CH$_3$)$_2$ | Ph | H | H | E | 8.28 (s, 1H); 7.60–7.00 (m, 10H); 3.89 (s, 3H); 3.74 (s, 3H); 3.10 (s, 6H) |
| 1.05 | N(CH$_3$)$_2$ | Ph | H | H | Z | 110–112° C. |
| 1.06 | OCH$_3$ | CH$_3$ | H | H | E | 107° C. |
| 1.07 | N(CH$_3$)$_2$ | CN | H | H | E | 8.23 (s, 1H); 7.51 (s, 1H); 7.48–7.25 (m, 4H); 3.87 (s, 3H); 3.75 (s, 3H); 3.12 (s, 6H); 97–98° C. |
| 1.08 | OCH$_3$ | Ph | H | H | E | 8.42 (s, 1H); 7.65–7.04 (m, 10H); 4.02 (s, 3H); 3.89 (s, 3H); 3.73 (s, 3H) |
| 1.09 | OCH$_3$ | CH$_3$ | CH$_3$ | H | E | 133–135° C. |
| 1.10 | OCH$_3$ | CH$_3$ | CH$_3$ | H | Z | 134–136° C. |
| 1.11 | OCH$_3$ | C$_4$H$_9$-t | H | H | E | 8.39 (s, 1H); 7.59 (s, 1H); 7.35–6.87 (m, 4H); 4.00 (s, 3H); 3.89 (s, 3H); 3.72 (s, 3H); 1.31 (s, 9H) |
| 1.12 | OCH$_3$ | C$_4$H$_9$-t | H | H | Z | 8.35 (s, 1H); 7.35–6.87 (m, 4H); 6.77 (s, 1H); 4.00 (s, 3H); 3.96 (s, 3H); 3.72 (s, 3H); 1.32 (s, 9H) |
| 1.13 | N(CH$_3$)$_2$ | C$_4$H$_9$-t | H | H | E | 8.24 (s, 1H); 7.49 (s, 1H); 7.31–6.80 (m, 4H); 3.87 (s, 3H); 3.73 (s, 3H); 3.08 (s, 6H); 1.30 (s, 9H) |
| 1.14 | OCH$_3$ | 2-CH$_3$-1,3-dioxolan-2-yl | H | H | E | 8.38 (s, 1H); 7.59 (s, 1H); 7.40–6.98 8M, 4H); 4.05–3.97 (m, 2H); 4.00 (s, 3H); 3.88 (s, 3H); 3.82–3.74 (m, 2H); 3.72 (s, 3H); 1.65 (s, 3H) |
| 1.15 | OCH$_3$ | 2-CH$_3$-1,3-dioxolan-2-yl | H | H | Z | 8.32 (s, 1H); 7.40–6.96 (m, 4H); 6.73 (s, 1H); 4.07–3.99 (m, 2H); 4.00 (s, 3H); 3.96 (s, 3H); 3.82–3.74 (m, 2H); 3.70 (s, 3H); 1.65 (s, 3H) |

TABLE 1-continued

Compounds of formula I ($R^5$ = H; X = CH; Y = $OCH_3$)

| Comp. No. | $R^1$ | $R^2$ | $R^3$ | $R^4$ | Isomer | physical data $^1$H—NMR or/and m.p. |
|---|---|---|---|---|---|---|
| 1.16 | $N(CH_3)_2$ | $-C(CH_3)=N-O-CH_2-CH=CH_2$ | H | H | E | 8.23 (s, 1H); 7.50 (s, 1H); 7.46–7.00 (m, 4H); 6.02 (ddd, 1H); 5.32 (d, 1H); 5.22 (d, 1H); 4.68 (d, 2H); 3.88 (s, 3H); 3.74 (s, 3H); 3.08 (s, 9H); 2.22 (s, 3H) |
| 1.17 | $OCH_3$ | $-C(CH_3)=$N-benzyloxy | H | H | E | 8.38 (s, 1H); 7.60 (s, 1H); 7.52–7.05 (m, 9H); 5.23 (s, 2H); 4.00 (s, 3H); 3.88 (s, 3H), 3.73 (s, 3H); 2.26 (s, 3H) |
| 1.18 | $OCH_3$ | 1,3-dioxan-2-yl | H | H | E | 8.38 (s, 1H); 7.57 (s, 1H); 7.40–7.02 (m, 4H); 5.50 (s, 1H); 4.30–4.20 (m, 4H); 4.02–3.90 (m, 4H); 3.95 (s, 3H); 3.88 (s, 3H); 3.72 (s, 3H); 2.30–2.10 (m, 1H); 1.48–1.37 (m, 1H) |
| 1.19 | —N-pyrrolidinyl | $C_3H_7$-i | H | H | E | 8.24 (s, 1H); 7.52 (s, 1H); 7.30–6.82 (m, 4H); 3.87 (s, 3H); 3.73 (s, 3H); 3.54–2.94 (m, 8H); 2.88 (dq, 1H); 1.98–1.82 (m, 8H); 1.24 (d, 6H); 100–102° C. |
| 1.20 | $N(CH_3)_2$ | phenoxy | H | H | E | 8.26 (s, 1H); 7.48 (s, 1H); 7.38–6.67 (m, 9H); 3.83 (s, 3H); 3.70 (s, 3H); 3.07 (6H) |
| 1.21 | $N(CH_3)_2$ | Cl | H | H | E | |
| 1.22 | $N(CH_3)_2$ | $-O-CH_2-CH=CH_2$ | H | H | E | |
| 1.23 | $N(CH_3)_2$ | $-O-CH_2-C\equiv CH$ | H | H | E | |
| 1.24 | $N(CH_3)_2$ | $-O-CH_2CH=CH-CH_3$ | H | H | E | |
| 1.25 | $N(CH_3)_2$ | $-O-CH_2-CH=C(CH_3)_2$ | H | H | E | |
| 1.26 | $N(CH_3)_2$ | benzyloxy | H | H | E | |
| 1.27 | $N(CH_3)_2$ | Cl | Cl | H | E | |
| 1.28 | $N(CH_3)_2$ | $CH_3$ | $CH_3$ | H | E | |
| 1.29 | $OCH_3$ | $-O-CH_2-CH=CH_2$ | H | H | E | |
| 1.30 | $OCH_3$ | $-O-CH_2-CH=CH-CH_3$ | H | H | E | |
| 1.31 | $OCH_3$ | $-O-CH_2-C\equiv CH$ | H | H | E | |
| 1.32 | $OCH_3$ | $-O-CH_2-CH=C(CH_3)_2$ | H | H | E | |
| 1.33 | $OCH_3$ | 1,3-dioxolan-2-yl | H | H | E | |
| 1.34 | $N(CH_3)_2$ | 1,3-dioxan-2-yl | H | H | E | |
| 1.35 | $N(CH_3)_2$ | 2-$CH_3$-dioxolan-2-yl | H | H | E | 102–103° C. |
| 1.36 | $N(CH_3)_2$ | 2,4,4-$(CH_3)_3$dioxolan-2-yl | H | H | E | |
| 1.37 | $N(CH_3)_2$ | $CH_3$ | H | H | E | 134–135° C. |
| 1.38 | $N(CH_3)_2$ | $CH_3$ | H | H | Z | 84–86° C. |
| 1.39 | $OCH_3$ | $C(CH_3)=CH_2$ | H | H | E | 90–92° C. |
| 1.40 | $OCH_3$ | $C_3H_7$-i | H | $CH_3$ | E | 100–102° C. |
| 1.41 | $OCH_3$ | phenoxy | H | H | E | 103–105° C. |
| 1.42 | $OCH_3$ | $-O-CH_2-CH=CH-Ph$ | H | H | | |
| 1.43 | $OCH_3$ | $-O-(CH_2)_3-Ph$ | H | H | | |
| 1.44 | $OCH_3$ | $-O-(CH_2)_2-Ph$ | H | H | | |
| 1.45 | $OCH_3$ | $-O-(CH_2)_2-O-Ph$ | H | H | | |
| 1.46 | $OCH_3$ | 2-$CH_3$-benzyloxy | H | H | | |
| 1.47 | $OCH_3$ | 2-$CH_3$-phenoxy | H | H | | |
| 1.48 | $OCH_3$ | 2-CN-phenoxy | H | H | | |
| 1.49 | $OCH_3$ | 2-Cl-phenoxy | H | H | | |
| 1.50 | $OCH_3$ | 2-Ph-thiazol-4-yl | H | H | | |
| 1.51 | $OCH_3$ | 3-$CH_3$-isoxazol-5-yl | H | H | | |
| 1.52 | $OCH_3$ | 3-$CF_3$-isoxazol-5-yl | H | H | | |
| 1.53 | $OCH_3$ | 3-Ph-isoxazol-5-yl | H | H | | |
| 1.54 | $OCH_3$ | 1-$CH_3$-3-Ph-pyrazol-5-yl | H | H | | |
| 1.55 | $OCH_3$ | 5-Ph-oxazol-2-yl | H | H | | |
| 1.56 | $OCH_3$ | 3-$CF_3$-benzyloxy | H | H | | |
| 1.57 | $OCH_3$ | $-O-(CH_2)_2-O-C_2H_5$ | H | H | | |
| 1.58 | $OCH_3$ | $-C(CH_3)=N-O-C_2H_5$ | H | H | | |
| 1.59 | $OCH_3$ | $-C(CH_3)=$N-3-Cl-benzyloxy | H | H | | |

TABLE 2

Compounds of formula I ($R^5$ = $CH_3$; X = CH; Y = $OCH_3$)

| Comp. No. | $R^1$ | $R^2$ | $R^3$ | $R^4$ | Isomer | physical data $^1$H-NMR or/and m.p. |
|---|---|---|---|---|---|---|
| 2.01 | $OCH_3$ | $C_3H_7$-i | H | $CH_3$ | E | 100–102° C. |
| 2.02 | $N(CH_3)_2$ | $C_3H_7$-i | H | H | E | |
| 2.03 | $OCH_3$ | $C_3H_7$-i | H | H | E | 7.55(s, 1H); 7.30–6.82(m, 4H); 3.96(s, 3H); 3.82(s, 3H); 3.68 (s, 3H); 2.90(dq, 1H); 2.42(s, 3H); 1.20(2d, 6H). |
| 2.04 | $OCH_3$ | $CF_3$ | H | H | E | 7.57(s, 1H); 7.50–7.23(m, 4H); 3.98(s, 3H); 3.83(s, 3H); 3.70 (s, 3H); 2.45(s, 3H). |
| 2.05 | $N(CH_3)_2$ | Ph | H | H | E | 110–112° C. |

TABLE 2-continued

Compounds of formula I ($R^5 = CH_3$; X = CH; Y = $OCH_3$)

| Comp. No. | $R^1$ | $R^2$ | $R^3$ | $R^4$ | Isomer | physical data $^1$H-NMR or/and m.p. |
|---|---|---|---|---|---|---|
| 2.06 | $OCH_3$ | $C(CH_3)$=N—$OCH_3$ | H | H | E | 78–80° C. |
| 2.07 | $N(CH_3)_2$ | $C_3H_7$-i | H | $CH_3$ | | |
| 2.08 | $OCH_3$ | 2-$CH_3$-benzyloxy | H | H | | |
| 2.09 | $OCH_3$ | —O—$(CH_2)_2$—Ph | H | H | | |
| 2.10 | $OCH_3$ | 2-Ph-thiazol-4-yl | H | H | | |
| 2.11 | $OCH_3$ | 3-$CF_3$-isoxazol-5-yl | H | H | | |
| 2.12 | $OCH_3$ | 3-$CH_3$-isoxazol-5-yl | H | H | | |
| 2.13 | $N(CH_3)_2$ | 3-$CF_3$-isoxazol-5-yl | H | H | E | TLC: Rf 0.13 hexane/ethyl acetate (2:1) |

TABLE 3

Compounds of formula I ($R^1 = N(CH_3)_2$; X = N; Y = $OCH_3$; E-form)

| Comp. No. | $R^2$ | $R^3$ | $R^4$ | $R^5$ | phys. data or $^1$H-NMR |
|---|---|---|---|---|---|
| 3.01 | —C—$(CH_3)$=N-4-Cl-benzyloxy | H | H | H | 8.23(s, 1H); 7.50–7.02(m, 3H); 5.18(s, 2H); 4.05 (s, 3H); 3.90(s, 3H); 3.14(s, 6H); 2.22(s, 3H). |
| 3.02 | —$C(CH_3)$=N-benzyloxy | H | H | H | 8.23(s, 1H); 7.52–7.02(m, 9H); 5.21(s, 2H); 4.05 (s, 3H); 3.90(s, 3H); 3.15(s, 6H); 2.23(s, 3H). |
| 3.03 | —$C(CH_3)$=N-3-Cl-benzyloxy | H | H | H | 8.22(s, 1H); 7.52–7.02(m, 8H); 5.18(s, 2H); 4.05 (s, 3H); 3.81(s, 3H); 7.15(s, 6H); 2.23(s, 3H). |
| 3.04 | —$C(CH_3)$=N—O—$C_2H_5$ | H | H | H | 8.22(s, 1H); 7.52–7.02(m, 4H); 4.22(q, 2H); 4.05 (s, 3H); 3.82(s, 3H); 3.14(s, 6H); 2.20(s, 3H); 1.30(t, 3H). |
| 3.05 | $CF_3$ | H | H | H | 8.22(s, 1H); 7.54–7.25(m, 4H); 4.06(s, 3H); 3.82 (s, 3H); 3.17(s, 6H) |
| 3.06 | —$C(CH_3)$=N—$OCH_3$ | H | H | H | 109–110° C. |
| 3.07 | —$C(CH_3)$=N—O—$CH_2$—$C(CH_3)$=$CH_2$ | H | H | H | 8.22(s, 1H); 7.52–7.02(m, 4H); 5.00(sbr, 1H); 4.92(sbr, 1H); 4.62(s, 2H); 4.06(s, 3H); 3.83(s, 3H); 3.16(s, 6H); 2.24(s, 3H); 1.78(s, 3H). |
| 3.08 | —$C(CH_3)$=N—$OCH_3$ | H | H | $CH_3$ | TLC: Rf 0.17 hexane/ethyl acetate (7:3) |
| 3.09 | $C_3H_7$-i | H | H | $CH_3$ | 7.26–6.83(m, 4H); 4.06(s, 3H); 3.85(s, 3H); 3.02 (s, 6H); 2.90(dq, 1H); 2.37(s, 3H); 1.22(2xd, 6H). |
| 3.10 | $C_3H_7$i | H | $CH_3$ | $CH_3$ | 7.27–6.66(m, 3H); 4.06(s, 3H); 3.84(s, 3H); 3.02 (s, 6H); 2.85(dq, 1H); 2.38(s, 3H); 2.32(s, 3H); 1.23(2xd, 6H). |
| 3.11 | $C_4H_9$-t | H | H | $CH_3$ | 7.29–6.83(m, 4H); 4.08(s, 3H); 3.85(s, 3H); 3.02 (s, 6H); 2.37(s, 3H); 1.30(s, 9H). |
| 3.12 | $C_4H_9$-t | H | H | H | 8.23(s, 1H); 7.26–6.83(m, 4H); 4.07(s, 3H); 3.84 (s, 3H); 3.03(s, 6H); 1.30(s, 9H). |
| 3.13 | Ph | H | H | $CH_3$ | 7.60–7.00(m, 9H); 4.05(s, 3H); 3.86(s, 3H); 3.02 (s, 6H); 2.38 (s, 3H). |
| 3.14 | 3,4-$(OCH_3)_2$—Ph | H | H | $CH_3$ | 7.30–6.83(m, 7H); 4.02(s, 3H); 3.86(s, 3H); 3.83 (s, 3H); 3.78(s, 3H); 2.97(s, 6H); 2.30(s, 3H). |
| 3.15 | 4-$OCH_3$—Ph | H | H | $CH_3$ | 108–110° C. |
| 3.16 | 3,5-$(CH_3)_2$-pyrazol-1-yl | H | H | $CH_3$ | 7.53–7.00(m, 4H); 5.98(s, 1H); 4.08(s, 1H); 3.85 (s, 3H); 3.02(s, 6H); 2.38(s, 3H); 2.32(s, 3H); 2.29(s, 3H). |
| 3.17 | 3-$CH_3$-isoxazol-5-yl | H | H | $CH_3$ | 7.48–7.00(m, 4H); 6.28(s, 1H); 4.00(s, 3H); 3.78 (s, 3H); 2.95(s, 6H); 2.26(s, 3H); 2.25(s, 3H). |
| 3.18 | 2-$CH_3$-phenoxy | H | H | $CH_3$ | 7.30–6.60(m, 8H); 4.03(s, 3H); 3.82(s, 3H); 3.02 (s, 6H); 2.38(s, 3H); 2.24(s, 3H). |
| 3.19 | 2-Cl-phenoxy | H | H | $CH_3$ | 7.48–6.68(m, 8H); 4.03(s, 3H); 3.82(s, 3H); 3.02 (s, 6H); 2.37(s, 3H). |
| 3.20 | 2-CN-phenoxy | H | H | H | 8.22(s, 1H); 7.67–6.82(m, 8H); 4.04(s, 3H); 3.80 (s, 3H); 3.13(s, 6H). |
| 3.21 | 2-$CH_3$-benzyloxy | H | H | $CH_3$ | 7.45–6.64(m, 8H); 5.00(s, 2H); 4.06(s, 3H); 3.85 (s, 3H); 3.02(s, 6H); 2.38(s, 3H); 2.37(s, 3H). |
| 3.22 | 2,4-$Cl_2$-benzyloxy | H | H | $CH_3$ | 7.52–6.65(m, 7H); 5.08(s, 2H); 4.05(s, 3H); 3.85 (s, 3H); 3.02(s, 6H); 2.38(s, 3H). |
| 3.23 | —O—$(CH_2)_2$—Ph | H | H | $CH_3$ | |
| 3.24 | 2-Ph-thiazol-4-yl | H | H | $CH_3$ | |
| 3.25 | 3-$CF_3$-isoxazol-5-yl | H | H | $CH_3$ | m.p. 97–99° C. |
| 3.26 | —$C(CH_3)$=N—O—$C_3H_7$-i | H | H | H | |
| 3.27 | —$C(CH_3)$=N—O—$C_3H_7$-i | H | H | $CH_3$ | |
| 3.28 | —$C(CH_3)$=N—O—$C_4H_9$-n | H | H | H | |
| 3.29 | —$C(CH_3)$=N—O—$C_4H_9$-n | H | H | $CH_3$ | |
| 3.30 | —$C(CH_3)$=N—O—$CH_2$—$C(CH_3)$=$CH_2$ | H | H | H | |
| 3.31 | —$C(CH_3)$=N—O—$CH_2$—CH=$CH_2$ | H | H | $CH_3$ | |
| 3.32 | —$C(CH_3)$=N—O—$CH_2$—C≡CH | H | H | H | |
| 3.33 | —$C(CH_3)$=N—O—$CH_2$—C≡CH | H | H | $CH_3$ | |
| 3.34 | —$C(CH_3)$=N—O—$C_2H_5$ | H | H | $CH_3$ | TLC: Rf 0.19 hexane/ethyl acetate (7:3) |

TABLE 3-continued

Compounds of formula I ($R^1$ = $N(CH_3)_2$; X = N; Y = $OCH_3$; E-form)

| Comp. No. | $R^2$ | $R^3$ | $R^4$ | $R^5$ | phys. data or $^1$H-NMR |
|---|---|---|---|---|---|
| 3.35 | —C($CH_3$)=N-benzyloxy | H | H | $CH_3$ | |
| 3.36 | —(CH_3)=N-3-Cl-benzyloxy | H | H | $CH_3$ | TLC: Rf 0.23 hexane/ethyl acetate (2:1) |
| 3.37 | —C($CH_3$)=N-4-Cl-benzyloxy | H | H | $CH_3$ | |
| 3.38 | —C($CH_3$)=N-2-Cl-benzyloxy | H | H | $CH_3$ | |
| 3.39 | —C($CH_3$)=N-2-$CH_3$-benzyloxy | H | H | $CH_3$ | |
| 3.40 | —C($CH_3$)=N-2,5-($CH_3$)$_2$-benzyloxy | H | H | $CH_3$ | |
| 3.41 | —C($CH_3$)=N—O—CH($CH_3$)-3-$CF_3$—Ph | H | H | $CH_3$ | |
| 3.42 | —C($CH_3$)=N-3-$CF_3$-benzyloxy | H | H | $CH_3$ | |
| 3.43 | —C($CH_3$)=N-3-$CF_3$-benzyloxy | H | H | H | |
| 3.44 | —C($CH_3$)=N—O—($CH_2$)$_2$-3-Cl—Ph | H | H | $CH_3$ | |
| 3.45 | —C($CH_3$)=N—O—($CH_2$)$_2$-4-Cl—Ph | H | H | $CH_3$ | |
| 3.46 | —C($CH_3$)=N—O—($CH_2$)$_2$—Ph | H | H | $CH_3$ | |
| 3.47 | $CF_3$ | H | H | $CH_3$ | |
| 3.48 | 3-Ph-5-$CH_3$-Pyrazol-1-yl | H | H | $CH_3$ | |
| 3.49 | 3-Ph-isoxazol-5-yl | H | H | $CH_3$ | |
| 3.50 | 3-Ph-1-$CH_3$-pyrazol-5-yl | H | H | $CH_3$ | |
| 3.51 | 3-$CF_3$-1-$CH_3$-pyrazol-5-yl | H | H | $CH_3$ | |
| 3.52 | 5-$CH_3$-oxazol-2-yl | H | H | $CH_3$ | |
| 3.53 | 5-Ph-oxazol-2-yl | H | H | $CH_3$ | |
| 3.54 | 5-$CF_3$-oxazol-2-yl | H | H | $CH_3$ | |
| 3.55 | 3-$CF_3$-benzyloxy | H | H | $CH_3$ | |
| 3.56 | —O—CH($CH_3$)-3-$CF_3$—Ph | H | H | $CH_3$ | |
| 3.57 | —O—($CH_2$)$_2$-$OCH_3$ | H | H | $CH_3$ | |
| 3.58 | —O—($CH_2$)$_2$—O—$C_2H_5$ | H | H | $CH_3$ | |
| 3.59 | —O—($CH_2$)$_2$—O—$C_4H_9$-n | H | H | $CH_3$ | |
| 3.60 | —O—($CH_2$)$_2$—O—Ph | H | H | $CH_3$ | |
| 3.61 | —C($CH_3$)=N—NH-6-Cl-2-pyridyl | H | H | $CH_3$ | |
| 3.62 | —C($CH_3$)=N—NH-6-Cl-2-pyridyl | H | H | H | |
| 3.63 | —C($CH_3$)=N—O-6-Cl-2-pyridyl | H | H | H | |
| 3.64 | —C($CH_3$)=N—O-6-Cl-2-pyridyl | H | H | $CH_3$ | |
| 3.65 | —C($CH_3$)=N—O-6-Br-2-pyridyl | H | H | | |
| 3.66 | —(CH_3)=N—O-6-Br-2-pyridyl | H | H | $CH_3$ | |
| 3.67 | —C($CH_3$)=N—NH-4,6-($CH_3$)$_2$-2-pyrimidinyl | H | H | $CH_3$ | |

TABLE 4

Compounds of formula I (X = N; Y = $NHCH_3$; E-form)

| Comp. No. | $R^1$ | $R^2$ | $R^3$ | $R^4$ | $R^5$ | m.p. |
|---|---|---|---|---|---|---|
| 4.01 | $OCH_3$ | —C($CH_3$)=N—$OCH_3$ | H | H | $CH_3$ | 122–124° C. |
| 4.02 | $N(CH_3)_2$ | H | H | H | $CH_3$ | 194° C. |
| 4.03 | $N(CH_3)_2$ | 3-$OCH_3$—Ph | H | H | $CH_3$ | 146–147° C. |
| 4.04 | $N(CH_3)_2$ | $C_3H_7$-i | H | H | $CH_3$ | 128–129° C. |
| 4.05 | $N(CH_3)_2$ | $C_3H_7$-i | H | $CH_3$ | $CH_3$ | 126° C. |
| 4.06 | $N(CH_3)_2$ | 2-Cl-phenoxy | H | H | $CH_3$ | 138–140° C. |
| 4.07 | $N(CH_3)_2$ | 2-$CH_3$-phenoxy | H | H | $CH_3$ | 142–143° C. |
| 4.08 | $N(CH_3)_2$ | 3,4-($OCH_3$)$_2$—Ph | H | H | $CH_3$ | 141–142° C. |
| 4.09 | $N(CH_3)_2$ | $C_4H_9$-t | H | H | H | 138° C. |
| 4.10 | $N(CH_3)_2$ | $C_4H_9$-t | H | H | $CH_3$ | 124–126° C. |
| 4.11 | $OCH_3$ | —C($CH_3$)=N-3-Cl-benzyloxy | H | H | H | |
| 4.12 | $OCH_3$ | —C($CH_3$)=N-3-Cl-benzyloxy | H | H | $CH_3$ | |
| 4.13 | $OCH_3$ | $C_3H_7$-i | H | $CH_3$ | $CH_3$ | |
| 4.14 | $OCH_3$ | Ph | H | H | H | |
| 4.15 | $OCH_3$ | 2-$CH_3$-phenoxy | H | H | $CH_3$ | |
| 4.16 | $OCH_3$ | 2-$CH_3$-benzyloxy | H | H | H | |
| 4.17 | $OCH_3$ | 3-$CF_3$-isoxazol-5-yl | H | H | H | |
| 4.18 | $OCH_3$ | 3-$CF_3$-isoxazol-5-yl | H | H | $CH_3$ | |
| 4.19 | $N(CH_3)_2$ | —C($CH_3$)=N-3-Cl-benzyloxy | H | H | H | |
| 4.20 | $N(CH_3)_2$ | —C($CH_3$)=N-3-Cl-benzyloxy | H | H | $CH_3$ | |
| 4.21 | $N(CH_3)_2$ | $CF_3$ | H | H | $CH_3$ | |
| 4.22 | $N(CH_3)_2$ | Ph | H | H | $CH_3$ | |
| 4.23 | $N(CH_3)_2$ | 3-$CF_2$-isoxazol-5-yl | H | H | H | |
| 4.24 | $N(CH_3)_2$ | 3-$CF_2$-isoxazol-5-yl | H | H | $CH_3$ | |
| 4.25 | $N(CH_3)_2$ | 2-Ph-thiazol-4-yl | H | H | $CH_3$ | |
| 4.26 | $N(CH_3)_2$ | —O—($CH_2$)$_2$—Ph | H | H | $CH_3$ | |

TABLE 5 compounds of formula I ($R^1$ = $OCH_3$; X = CH; Y = $OCH_3$)

| Comp. No. | $R^2$ | $R^3$ | $R^4$ | $R^5$ | physical data or $^1$H-NMR |
|---|---|---|---|---|---|
| 5.01 | 2-$CH_3$-benzyloxy | H | H | H | 8.40(s, 1H); 7.58(s, 1H); 7.40–6.65(m, 8H); 5.00(s, 2H); 3.98(s, 3H); 3.85(s, 3H); 3.70(s, 3H); 2.35(s, 3H). |
| 5.02 | 3-$NO_2$—Ph | H | H | H | 8.48–7.11(m, 10H); 4.00(s, 3H); 3.88(s, 3H); 3.72(s, 3H). |
| 5.03 | 3-Cl-benzyloxy | H | H | H | 8.40(s, 1H); 7.58(s, 1H); 7.45–6.68(m, 8H); 5.02(s, 2H); 3.98(s, 3H); 3.85(s, 3H); 3.71(s, 3H). |
| 5.04 | —O—$(CH_2)_2$—Ph | H | H | H | 8.40(s, 1H); 7.58(s, 1H); 7.32–6.61(m, 9H); 3.95(s, 3H); 3.85(s, 3H); 3.70(s, 3H). |
| 5.05 | 2,5-$(CH_3)_2$—Ph | H | H | H | 8.40(s, 1H); 7.60(s, 1H); 7.48–7.00(m, 7H); 3.98(s, 3H); 3.85(s, 3H); 3.75(s, 3H); 2.35(s, 3H); 2.25(s, 3H). |
| 5.06 | 3-$C_2H_5$-isoxazol-5-yl | H | H | H | 8.39(s, 1H); 7.62–7.10(m, 5H); 6.49(s, 1H); 3.99(S, 3H); 3.89(s, 3H); 3.72(s, 3H); 2.72(q, 2H); 1.30(t, 3H). |
| 5.07 | 3-$C_4H_9$-n-isoxazol-5-yl | H | H | H | 8.39(s, 1H); 7.62–7.10(m, 5H); 6.45(s, 1H); 4.00(s, 3H); 3.89(s, 3H); 3.72(s, 3H); 3.70(t, 2H); 2.75–2.25(m, 4H); 0.95(t, 3H). |
| 5.08 | 2-CN-phenoxy | H | H | H | 8.40(s, 1H); 7.70–6.80(m, 8H); 3.95(s, 3H); 3.85(s, 3H); 3.70(s, 3H); 7.59(s, 1H). |
| 5.09 | 2-naphthyl | H | H | H | 8.42(s, 1H); 8.05–7.05(s, 11H); 4.00(s, 3H); 3.85(s, 3H); 3.75(s, 3H); 7.60(s, 1H). |
| 5.10 | 2-Ph-thiazol-4-yl | H | H | H | 8.40(s, 1H); 8.05–7.05(m, 1oH); 3.95(s, 3H); 3.90(s, 5H); 3.75(s, 3H); 7.60(s, 1H). |
| 5.11 | —C($CH_3$)=N-3,4-$Cl_2$-benzyloxy | H | H | H | 8.39(s, 1H); 7.50–7.01(m, 7H); 5.18(s, 2H); 3.98(s, 3H); 3.85(s, 3H); 3.71(s, 3H); 2.25(s, 3H): 7.59(s, 1H). |
| 5.12 | —C($CH_3$)=N-3-Cl-benzyloxy | H | H | H | 8.39(s, 1H); 7.50–7.02(m, 8H); 5.18(s, 2H); 3.98(s, 3H); 3.85(s, 3H); 3.71(s, 3H); 2.25(s, 3H); 7.60(s, 1H). |
| 5.13 | —C($CH_3$)=N-2-$CH_3$-benzyloxy | H | H | H | 8.36(s, 1H); 7.52–7.02(m, 8H); 5.22(s, 2H); 3.98(s, 3H); 3.85(s, 3H); 3.70(s, 3H); 2.38(s, 3H); 2.25(s, 3H); 7.58(s, 1H). |
| 5.14 | 3-Cl-benzyloxy | H | H | H | 8.40(s, 1H); 7.45–6.68(m 8H); 5.02(s, 2H); 3.95(s, 3H); 3.85(s, 3H); 3.70(s, 3H); 7.58(s, 1H). |
| 5.15 | —C($CH_3$)=N—$OCH_3$ | H | H | H | |
| 5.16 | —C($CH_3$)=N—$OCH_3$ | H | H | $CH_3$ | |
| 5.17 | —C($CH_3$)=N—O—$C_3H_7$-i | H | H | H | |
| 5.18 | —C($CH_3$)=N—O—$C_3H_7$-i | H | H | $CH_3$ | |
| 5.19 | —C($CH_3$)=N—O—$C_4H_9$-n | H | H | H | |
| 5.20 | —C($CH_3$)=N—O—$C_4H_9$-n | H | H | $CH_3$ | |
| 5.21 | —C($CH_3$)=N-3-$CF_3$-benzyloxy | H | H | H | |
| 5.22 | —C($CH_3$)=N-3-$CF_3$-benzyloxy | H | H | $CH_3$ | |
| 5.23 | —C($CH_3$)=N—O—CH($CH_3$)-3-$CF_3$—Ph | H | H | H | |
| 5.24 | —C($CH_3$)=N—O—CH($CH_3$)-3-$CF_3$—Ph | H | H | $CH_3$ | |
| 5.25 | —C($CH_3$)=N—O—$(CH_2)_2$—Ph | H | H | H | |
| 5.26 | —C($CH_3$)=N—O—$(CH_2)_2$—Ph | H | H | $CH_3$ | |
| 5.27 | —C($CH_3$)=N—O—$(CH_2)_2$-4-Cl—Ph | H | H | H | |
| 5.28 | —C($CH_3$)=N—O—$(CH_2)_2$-4-Cl—Ph | H | H | $CH_3$ | |
| 5.29 | 3-Ph-5-$CH_3$-pyrazol-1-yl | H | H | H | |
| 5.30 | 3-Ph-5-$CH_3$-pyrazol-1-yl | H | H | $CH_3$ | |
| 5.31 | 3-Ph-1-$CH_3$-pyrazol-5-yl | H | H | H | |
| 5.32 | 3-Ph-1-$CH_3$-pyrazol-5-yl | H | H | $CH_3$ | |
| 5.33 | 3-$CH_3$-isoxazol-5-yl | H | H | $CH_3$ | |
| 5.34 | 3-$CH_3$-isoxazol-5-yl | H | H | H | 8.40(s, 1H); 7.70–7.20(m, 4H); 6.98(s, 1H); 6.75(s, 1H); 4.02(s, 3H); 3.92(s, 3H); 3.74(s, 3H). |
| 5.35 | 3-$CF_3$-isoxazol-5-yl | H | H | $CH_3$ | |
| 5.36 | 3-Ph-isoxazol-5-yl | H | H | $CH_3$ | |
| 5.37 | 5-Ph-oxazol-2-yl | H | H | $CH_3$ | |
| 5.38 | $C_3H_7$-i | H | H | $CH_3$ | |
| 5.39 | $CF_3$ | H | H | $CH_3$ | |
| 5.40 | $C_4H_9$-n | H | H | $CH_3$ | |
| 5.41 | $C_4H_9$-i | H | $CH_3$ | $CH_3$ | |
| 5.42 | phenoxy | H | H | $CH_3$ | |
| 5.43 | 2-$CH_3$-phenoxy | H | H | $CH_3$ | |
| 5.44 | 2-CN-phenoxy | H | H | $CH_3$ | |
| 5.45 | 2-Cl-phenoxy | H | H | $CH_3$ | |
| 5.46 | 2-$CH_3$-benzyloxy | H | H | $CH_3$ | |
| 5.47 | 2-Cl-benzyloxy | H | H | $CH_3$ | |
| 5.48 | 3-Cl-benzyloxy | H | H | $CH_3$ | |
| 5.49 | 3-$CF_3$-benzyloxy | H | H | $CH_3$ | |
| 5.50 | —O—CH($CH_3$)-3-$CF_3$—Ph | H | H | $CH_3$ | |

TABLE 5-continued compounds of formula I ($R^1$ = $OCH_3$; X = CH; Y = $OCH_3$)

| Comp. No. | $R^2$ | $R^3$ | $R^4$ | $R^5$ | physical data or $^1$H-NMR |
|---|---|---|---|---|---|
| 5.51 | —O—$(CH_2)_2$—Ph | H | H | $CH_3$ | |
| 5.52 | —O—$CH_2$—CH=CH—Ph | H | H | $CH_3$ | |
| 5.53 | —O—$(CH_2)_3$—Ph | H | H | $CH_3$ | |
| 5.54 | —O—$(CH_2)_2$—O—$C_2H_5$ | H | H | $CH_3$ | |
| 5.55 | —O—$(CH_2)_2$—O—Ph | H | H | $CH_3$ | |
| 5.56 | Ph | H | H | $CH_3$ | |
| 5.57 | —C($CH_3$)=N—NH-6-Cl-2-pyridyl | H | H | $CH_3$ | |
| 5.58 | —C($CH_3$)=N—O-6-Cl-2-pyridyl | H | H | $CH_3$ | |
| 5.59 | —C($CH_3$)=N—O-6-Br-2-pyridyl | H | H | $CH_3$ | |
| 5.60 | —C($CH_3$)=N—NH-4,6-$(CH_3)_2$-2-pyrimidinyl | H | H | $CH_3$ | |

TABLE 6

Compounds of formula I ($R^1$ = $OCH_3$; X = N; Y = $OCH_3$)

| Comp. No. | $R^2$ | $R^3$ | $R^4$ | $R_5$ | physical data or $^1$H-NMR |
|---|---|---|---|---|---|
| 6.01 | 2-$CH_2$-benzyloxy | H | H | H | 8.45(s, 1H); 7.60–6.65(m, 8H); 5.02(s, 2H); 4.12(s, 3H); 4.00(s, 3H); 3.85(s, 3H); 2.35(s, 3H). |
| 6.02 | 2-Ph-thiazol-4-yl | H | H | H | 8.41(s, 1H); 8.05–7.05(m, 10H); 4.12 and 4.05 (2s, 3H); 3.99 and 3.95(2s, 3H); 3.85 and 3.40 (2s, 3H). |
| 6.03 | —C($CH_3$)=N-2-$CH_3$-benzyloxy | H | H | H | 8.40(s, 1H); 7.55–7.03(m, 9H); 5.25(s, 2H); 4.10(s, 3H); 4.05(s, 3H); 3.80(s, 3H). |
| 6.04 | —C($CH_3$)=N-3-Cl-benzyloxy | H | H | H | 8.38(s, 1H); 7.55–7.02(m, 8H); 5.18(s, 2H); 4.08(s, 3H); 4.02(s, 3H); 3.80(s, 3H); 2.25(s, 3H). |
| 6.05 | 3-Ph-isoxazol-5-yl | H | H | $CH_3$ | |
| 6.06 | 3-Ph-1-$CH_3$-pyrazol-5-yl | H | H | $CH_3$ | |
| 6.07 | —C($CH_3$)=N-3,4-$Cl_2$-benzyloxy | H | H | H | 8.38(s, 1H); /.55–7.05(m, 7H); 5.15(s, 2H); 4.08 (s, 3H); 4.04(s, 3H); 3.81(s, 3H); 2.24(s, 3H). |
| 6.08 | 2-Ph-thiazol-4-yl | H | H | H | |
| 6.09 | 2,5-$(CH_3)_2$—Ph | H | H | H | 8.40(s, 1H); 7.50–7.00(m, 7H); 4.09(s, 3H); 4.05(s, 3H); 3.81(s, 3H); 3.32(s, 3H); 3.24(s, 3H). |
| 6.10 | 2-Ph-thiazol-4-yl | H | H | $CH_3$ | |
| 6.11 | 3-$C_4H_9$-n-isoxazol-5-yl | H | H | H | 8.39(s, 1H); 7.70–7.12(m, 5H); 6.39(s, 1H); 4.10(s, 3H); 4.05(s, 3H); 3.45(s, 3H); 2.70(t, 2H); 1.85–1.20(m, 4H); 0.95(t, 3H). |
| 6.12 | 2-Ph-oxazol-2-yl | H | H | $CH_3$ | |
| 6.13 | 3-$C_2H_5$-isoxazol-5-yl | H | H | H | 8.40(s, 1H); 7.69–7.12(m, 4H); 6.40(s, 1H); 4.10(s, 3H); 4.04(s, 3H); 2.75(q, 2H); 1.30(t, 3H). |
| 6.14 | 3-$C_3H_7$-n-isoxazol-5-yl | H | H | H | 8.40(s, 1H); 7.62–7.11(m, 4H); 6.38(s, 1H); 4.00(s, 3H); 3.90(s, 3H); 3.74(s, 3H); 2.60(t, 2H); 1.72(q, 2H); 1.00(t, 3H). |
| 6.15 | —C($CH_3$)=N—$OCH_3$ | H | H | H | |
| 6.16 | —C($CH_3$)=N—$OCH_3$ | H | H | $CH_3$ | 7.52–7.04(m, 4H); 4.06(s, 3H); 4.00(s, 3H); 3.99(s, 3H); 3.80(s, 3H); 2.40(s, 3H); 2.20(s, 3H). |
| 6.17 | —C($CH_3$)=N—$OC_2H_5$ | H | H | H | |
| 6.18 | —C($CH_3$)=N—$OC_2H_5$ | H | H | $CH_3$ | |
| 6.19 | —C($CH_3$)=N-3-Cl-benzyloxy | H | H | $CH_3$ | |
| 6.20 | Ph | H | H | $CH_3$ | |
| 6.21 | $CF_3$ | H | H | H | |
| 6.22 | $CF_3$ | H | H | $CH_3$ | |
| 6.23 | $C_3H_7$-i | H | $CH_3$ | $CH_3$ | |
| 6.24 | 2-$CH_3$-phenoxy | H | H | $CH_3$ | |
| 6.25 | 2-CN-phenoxy | H | H | H | |
| 6.26 | 2-CN-phenoxy | H | H | $CH_3$ | |
| 6.27 | 2-$CH_3$-benzyloxy | H | H | $CH_3$ | 8.48(s, 1H); 7.92–6.68(m, 8H); 5.02(s, 2H); 4.15(s, 3H); 4.04(s, 3H); 3.92(s, 3H); 2.38(s, 3H). |
| 6.28 | 3-$CF_3$-benzyloxy | H | H | $CH_3$ | |
| 6.29 | —O—$(CH_2)_2$—Ph | H | H | H | |
| 6.30 | —O—$(CH_2)_2$—Ph | H | H | $CH_3$ | |
| 6.31 | 3-$CF_3$-isoxazol-5-yl | H | H | H | |
| 6.32 | 3-$CF_3$-isoxazol-5-yl | H | H | $CH_3$ | |
| 6.33 | —C($CH_3$)=N—NH-6-Cl-2-pyridyl | H | H | H | |
| 6.34 | —C($CH_3$)=N—NH-6-Cl-2-pyridyl | H | H | $CH_3$ | |
| 6.35 | —C($CH_3$)=N—O-6-Cl-2-pyridyl | H | H | H | |

TABLE 6-continued

Compounds of formula I ($R^1$ = $OCH_3$; X = N; Y = $OCH_3$)

| Comp. No. | $R^2$ | $R^3$ | $R^4$ | $R_5$ | physical data or $^1$H-NMR |
|---|---|---|---|---|---|
| 6.36 | —C($CH_3$)=N—O-6-Cl-2-pyridyl | H | H | $CH_3$ | |
| 6.37 | —C($CH_3$)=N—O-6-Br-2-pyridyl | H | H | H | |
| 6.38 | —C($CH_3$)=N—NH—4,6-($CH_3$)$_2$-2-pyrimidinyl | H | H | $CH_3$ | |

TABLE 7

Compounds of formula II

| Comp. No. | $R^1$ | $R^2$ | $R^3$ | $R^4$ | $R^5$ | X | physical data or $^1$H-NMR |
|---|---|---|---|---|---|---|---|
| 7.01 | $OCH_3$ | $C_3H_7$-i | H | H | H | CH | |
| 7.02 | $OCH_3$ | $CF_3$ | H | H | H | CH | |
| 7.03 | N($CH_3$)$_2$ | Ph | H | H | H | CH | |
| 7.04 | $OCH_3$ | $CH_3$ | H | H | H | CH | |
| 7.05 | N($CH_3$)$_2$ | CN | H | H | H | CH | |
| 7.06 | $OCH_3$ | Ph | H | H | H | CH | |
| 7.07 | $OCH_3$ | $CH_3$ | $CH_3$ | H | H | CH | |
| 7.08 | $OCH_3$ | $C_4H_9$-t | H | H | H | CH | |
| 7.09 | N($CH_3$)$_2$ | $C_4H_9$-t | H | H | H | CH | |
| 7.10 | $OCH_3$ | 2-$CH_3$-1,3-dioxolan-2-yl | H | H | H | CH | |
| 7.11 | N($CH_3$)$_2$ | —C($CH_3$)=N—O—$CH_2$—CH=$CH_2$ | H | H | H | CH | |
| 7.12 | $OCH_3$ | —C($CH_3$)=N—benzyloxy | H | H | H | CH | |
| 7.13 | $OCH_3$ | 1,3-dioxan-2-yl | H | H | H | CH | |
| 7.14 | —N—pyrrolidinyl | $C_3H_7$-i | H | H | H | CH | |
| 7.15 | N($CH_3$)$_2$ | phenoxy | H | H | H | CH | |
| 7.16 | N($CH_3$)$_2$ | Cl | H | H | H | CH | |
| 7.17 | N($CH_3$)$_2$ | —O—$CH_2$—CH=$CH_2$ | H | H | H | CH | |
| 7.18 | N($CH_3$)$_2$ | —O—$CH_2$—C≡CH | H | H | H | CH | |
| 7.19 | N($CH_3$)$_2$ | —O—$CH_2$CH=CH—$CH_3$ | H | H | H | CH | |
| 7.20 | N($CH_3$)$_2$ | —O—$CH_2$—CH=C($CH_3$)$_2$ | H | H | H | CH | |
| 7.21 | N($CH_3$)$_2$ | benzyloxy | H | H | H | CH | |
| 7.22 | N($CH_3$)$_2$ | Cl | Cl | H | H | CH | |
| 7.23 | N($CH_3$)$_2$ | $CH_3$ | $CH_3$ | H | H | CH | |
| 7.24 | $OCH_3$ | —O—$CH_2$—CH=$CH_2$ | H | H | H | CH | |
| 7.25 | $OCH_3$ | —O—$CH_2$—CH=CH—$CH_3$ | H | H | H | CH | |
| 7.26 | $OCH_3$ | —O—$CH_2$—C≡CH | H | H | H | CH | |
| 7.27 | $OCH_3$ | —O—$CH_2$—CH=C($CH_3$)$_2$ | H | H | H | CH | |
| 7.28 | $OCH_3$ | 1,3-dioxolan-2-yl | H | H | H | CH | |
| 7.29 | N($CH_3$)$_2$ | 1,3-dioxan-2-yl | H | H | H | CH | |
| 7.30 | N($CH_3$)$_2$ | 2-$CH_3$-dioxolan-2-yl | H | H | H | CH | |
| 7.31 | N($CH_3$)$_2$ | 2,4,4-($CH_3$)$_3$dioxolan-2-yl | H | H | H | CH | |
| 7.32 | N($CH_3$)$_2$ | $CH_3$ | H | H | H | CH | |
| 7.33 | $OCH_3$ | C($CH_3$)=$CH_2$ | H | H | H | CH | |
| 7.34 | $OCH_3$ | $C_3H_7$-i | H | $CH_3$ | H | CH | |
| 7.35 | $OCH_3$ | phenoxy | H | H | H | CH | |
| 7.36 | $OCH_3$ | —O—$CH_2$—CH=CH—Ph | H | H | H | CH | |
| 7.37 | $OCH_3$ | —O—($CH_2$)$_3$—Ph | H | H | H | CH | |
| 7.38 | $OCH_3$ | —O—($CH_2$)$_2$—Ph | H | H | H | CH | |
| 7.39 | $OCH_3$ | —O—($CH_2$)$_2$—O—Ph | H | H | H | CH | |
| 7.40 | $OCH_3$ | 2-$CH_3$-benzyloxy | H | H | H | CH | |
| 7.41 | $OCH_3$ | 2-$CH_3$-phenoxy | H | H | H | CH | |
| 7.42 | $OCH_3$ | 2-CN-phenoxy | H | H | H | CH | |
| 7.43 | $OCH_3$ | 2-Cl-phenoxy | H | H | H | CH | |
| 7.44 | $OCH_3$ | 2-Ph-thiazol-4-yl | H | H | H | CH | |
| 7.45 | $OCH_3$ | 3-Ph-isoxazol-5-yl | H | H | H | CH | |
| 7.46 | $OCH_3$ | 1-$CH_3$-3-Ph-pyrazol-5-yl | H | H | H | CH | |
| 7.47 | $OCH_3$ | 5-Ph-oxazol-2-yl | H | H | H | CH | |
| 7.48 | $OCH_3$ | 3-$CF_3$-benzyloxy | H | H | H | CH | |
| 7.49 | $OCH_3$ | —O—($CH_2$)$_2$—O—$C_2H_5$ | H | H | H | CH | |
| 7.50 | $OCH_3$ | —C($CH_3$)=N—O—$C_2H_5$ | H | H | H | CH | |
| 7.51 | $OCH_3$ | —C($CH_3$)=N-3-Cl-benzyloxy | H | H | H | CH | |
| 7.52 | $OCH_3$ | $C_3H_7$-i | H | $CH_3$ | $CH_3$ | CH | |
| 7.53 | N($CH_3$)$_2$ | $C_3H_7$-i | H | H | $CH_3$ | CH | |
| 7.54 | $OCH_3$ | $C_3H_7$-i | H | H | $CH_3$ | CH | |
| 7.55 | $OCH_3$ | $CF_3$ | H | H | $CH_3$ | CH | |
| 7.56 | N($CH_3$)$_2$ | Ph | H | H | $CH_3$ | CH | |

TABLE 7-continued

Compounds of formula II

| Comp. No. | R¹ | R² | R³ | R⁴ | R⁵ | X | physical data or ¹H-NMR |
|---|---|---|---|---|---|---|---|
| 7.57 | OCH₃ | C(CH₃)=NOCH₃ | H | H | CH₃ | CH | |
| 7.58 | N(CH₃)₂ | C₃H₇-i | H | CH₃ | CH₃ | CH | |
| 7.59 | OCH₃ | 2-CH₃-benzyloxy | H | H | CH₃ | CH | |
| 7.60 | OCH₃ | —O—(CH₂)₂—Ph | H | H | CH₃ | CH | |
| 7.61 | OCH₃ | 2-Ph-thiazol-4-yl | H | H | CH₃ | CH | |
| 7.62 | OCH₃ | 3-CF₃-isoxazol-5-yl | H | H | CH₃ | CH | |
| 7.63 | OCH₃ | 3-CH₃-isoxazol-5-yl | H | H | CH₃ | CH | |
| 7.64 | N(CH₃)₂ | —C(CH₃)=N-4-Cl-benzyloxy | H | H | H | N | |
| 7.65 | N(CH₃)₂ | —C(CH₃)=N-benzyloxy | H | H | H | N | |
| 7.66 | N(CH₃)₂ | —C(CH₃)=N-3-Cl-benzyloxy | H | H | H | N | 10.20(s, 1H);8.28(s, 1H);7.52–7.02 (m, 9H);5.22(s, 2H);3.87(s, 3H); 3.07(s, 6H);2.23(s, 3H). |
| 7.67 | N(CH₃)₂ | —C(CH₃)=N—O—C₂H₅ | H | H | H | N | |
| 7.68 | N(CH₃)₂ | CF₃ | H | H | H | N | |
| 7.69 | N(CH₃)₂ | —C(CH₃)=N—OCH₃ | H | H | H | N | |
| 7.70 | N(CH₃)₂ | —C(CH₃)=N—O—CH₂—C(CH₃)=CH₂ | H | H | H | N | |
| 7.71 | N(CH₃)₂ | —C(CH₃)=N—OCH₃ | H | H | CH₃ | N | |
| 7.72 | N(CH₃)₂ | C₃H₇-i | H | H | CH₃ | N | |
| 7.73 | N(CH₃)₂ | C₃H₇-i | H | CH₃ | CH₃ | N | |
| 7.74 | N(CH₃)₂ | C₄H₉-t | H | H | CH₃ | N | |
| 7.75 | N(CH₃)₂ | C₄H₉-t | H | H | H | N | |
| 7.76 | N(CH₃)₂ | Ph | H | H | CH₃ | N | |
| 7.77 | N(CH₃)₂ | 3,4-(OCH₃)₂—Ph | H | H | CH₃ | N | 9.88(s, 1H);7.40–6.88(m, 7H);3.92 (s, 3H);3.90(s, 3H);3.83(s, 3H); 3.02(s, 6H);2.38(s, 3H);2.36(s, 3H). |
| 7.78 | N(CH₃)₂ | 4-OCH₃—Ph | H | H | CH₃ | N | |
| 7.79 | N(CH₃)₂ | 3,5-(CH₃)₂-pyrazol-1-yl | H | H | CH₃ | N | |
| 7.80 | N(CH₃)₂ | 3-CH₃-isoxazol-5-yl | H | H | CH₃ | N | 9.15(s, 1H);7.67–7.10(m, 4H);6.33 (s, 1H);3.87(s, 3H);3.06(s, 6H): 2.36(s, 3H);2.34(s, 3H). |
| 7.81 | N(CH₃)₂ | 2-CH₃-phenoxy | H | H | CH₃ | N | |
| 7.82 | N(CH₃)₂ | 2-Cl-phenoxy | H | H | CH₃ | N | |
| 7.83 | N(CH₃)₂ | 2-CN-phenoxy | H | H | H | N | |
| 7.84 | N(CH₃)₂ | 2-CH₃-benzyloxy | H | H | CH₃ | N | |
| 7.85 | N(CH₃)₂ | 2,4-Cl₂-benzyloxy | H | H | CH₃ | N | |
| 7.86 | N(CH₃)₂ | —O—(CH₂)₂—Ph | H | H | CH₃ | N | |
| 7.87 | N(CH₃)₂ | 2-Ph-thiazol-4-yl | H | H | CH₃ | N | |
| 7.88 | N(CH₃)₂ | 3-CF₃-isoxazol-5-yl | H | H | CH₃ | N | |
| 7.89 | N(CH₃)₂ | —C(CH₃)=N—O—C₃H₇-i | H | H | H | N | |
| 7.90 | N(CH₃)₂ | —C(CH₃)=N—O—C₃H₇-i | H | H | CH₃ | N | |
| 7.91 | N(CH₃)₂ | —C(CH₃)=N—O—C₄H₉-n | H | H | H | N | |
| 7.92 | N(CH₃)₂ | —C(CH₃)=N—O—C₄H₉-n | H | H | CH₃ | N | |
| 7.93 | N(CH₃)₂ | —C(CH₃)=N—O—CH₂—C(CH₃)=CH₂ | H | H | H | N | |
| 7.94 | N(CH₃)₂ | —C(CH₃)=N—O—CH₂—CH=CH₂ | H | H | CH₃ | N | |
| 7.95 | N(CH₃)₂ | —C(CH₃)=N—O—CH₂—C≡CH | H | H | H | N | |
| 7.96 | N(CH₃)₂ | —C(CH₃)=N—O—CH₂—C≡CH | H | H | CH₃ | N | |
| 7.97 | N(CH₃)₂ | —C(CH₃)=N—O—C₂H₅ | H | H | CH₃ | N | |
| 7.98 | N(CH₃)₂ | —C(CH₃)=N-benzyloxy | H | H | CH₃ | N | |
| 7.99 | N(CH₃)₂ | —C(CH₃)=N-3-Cl-benzyloxy | H | H | CH₃ | N | |
| 7.100 | N(CH₃)₂ | —C(CH₃)=N-4-Cl-benzyloxy | H | H | CH₃ | N | |
| 7.101 | N(CH₃)₂ | —C(CH₃)=N-2-Cl-benzyloxy | H | H | CH₃ | N | |
| 7.102 | N(CH₃)₂ | —C(CH₃)=N-2-CH₃-benzyloxy | H | H | CH₃ | N | |
| 7.103 | N(CH₃)₂ | —C(CH₃)=N-2,5-(CH₃)₂-benzyloxy | H | H | CH₃ | N | |
| 7.104 | N(CH₃)₂ | —C(CH₃)=N—O—CH(CH₃)-3-CF₃-Ph | H | H | CH₃ | N | |
| 7.105 | N(CH₃)₂ | —C(CH₃)=N-3-CF₃-benzyloxy | H | H | CH₃ | N | |
| 7.106 | N(CH₃)₂ | —C(CH₃)=N-3-CF₃-benzyloxy | H | H | H | N | |
| 7.107 | N(CH₃)₂ | —C(CH₃)=N—O—(CH₂)₂-3-Cl—Ph | H | H | CH₃ | N | |
| 7.108 | N(CH₃)₂ | —C(CH₃)=N—O—(CH₂)₂-4-Cl—Ph | H | H | CH₃ | N | |
| 7.109 | N(CH₃)₂ | 3-Ph-5-CH₃-pyrazol-1-yl | H | H | CH₃ | N | |
| 7.110 | N(CH₃)₂ | 3-Ph-isoxazol-5-yl | H | H | CH₃ | N | |
| 7.111 | N(CH₃)₂ | 3-Ph-1-CH₃-pyrazol-5-yl | H | H | CH₃ | N | |
| 7.112 | N(CH₃)₂ | 3-CF₃-1-CH₃-pyrazol-5-yl | H | H | CH₃ | N | |
| 7.113 | N(CH₃)₂ | 5-CH₃-oxazol-2-yl | H | H | CH₃ | N | |
| 7.114 | N(CH₃)₂ | 5-Ph-oxazol-2-yl | H | H | CH₃ | N | |
| 7.115 | N(CH₃)₂ | 5-CF₃-oxazol-2-yl | H | H | CH₃ | N | |
| 7.116 | N(CH₃)₂ | 3-CF₃-benzyloxy | H | H | CH₃ | N | |
| 7.117 | N(CH₃)₂ | —O—CH(CH₃)—3-CF₃—Ph | H | H | CH₃ | N | |
| 7.118 | N(CH₃)₂ | —O—(CH₂)₂—OCH₃ | H | H | CH₃ | N | |
| 7.119 | N(CH₃)₂ | —O—(CH₂)₂—O—C₂H₅ | H | H | CH₃ | N | |
| 7.120 | N(CH₃)₂ | —O—(CH₂)₂—O—C₄H₉-n | H | H | CH₃ | N | |
| 7.121 | N(CH₃)₂ | —O—(CH₂)₂—O—Ph | H | H | CH₃ | N | |

TABLE 7-continued

Compounds of formula II

| Comp. No. | R¹ | R² | R³ | R⁴ | R⁵ | X | physical data or ¹H-NMR |
|---|---|---|---|---|---|---|---|
| 7.122 | OCH₃ | 2-CH₃-benzyloxy | H | H | H | CH | |
| 7.123 | OCH₃ | 3-NO₂—Ph | H | H | H | CH | |
| 7.124 | OCH₃ | 3-Cl-benzyloxy | H | H | H | CH | |
| 7.125 | OCH₃ | —O—(CH₂)₂—Ph | H | H | H | CH | |
| 7.126 | OCH₃ | 2,5-(CH₃)₂—Ph | H | H | H | CH | |
| 7.127 | OCH₃ | 3-C₂H₅-isoxazol-5-yl | H | H | H | CH | |
| 7.128 | OCH₃ | 3-C₄H₉-n-isoxazol-5-yl | H | H | H | CH | |
| 7.129 | OCH₃ | 2-CN-phenoxy | H | H | H | CH | |
| 7.130 | OCH₃ | 2-naphthyl | H | H | H | CH | |
| 7.131 | OCH₃ | 2-Ph-thiazol-4-yl | H | H | H | CH | |
| 7.132 | OCH₃ | —C(CH₃)=N-3,4-Cl₂-benzyloxy | H | H | H | CH | |
| 7.133 | OCH₃ | —C(CH₃)=N-3-Cl-benzyloxy | H | H | H | CH | |
| 7.134 | OCH₃ | —C(CH₃)=N-3-CH₃-benzyloxy | H | H | H | CH | |
| 7.135 | OCH₃ | 3-Cl-benzyloxy | H | H | H | CH | |
| 7.136 | OCH₃ | —C(CH₃)=N—OCH₃ | H | H | H | CH | |
| 7.137 | OCH₃ | —C(CH₃)=N—OCH₃ | H | H | CH₃ | CH | |
| 7.138 | OCH₃ | —C(CH₃)=N—O—C₃H₇-i | H | H | H | CH | |
| 7.139 | OCH₃ | —C(CH₃)=N—O—C₃H₇-i | H | H | CH₃ | CH | |
| 7.140 | OCH₃ | —C(CH₃)=N—O—C₄H₉-n | H | H | H | CH | |
| 7.141 | OCH₃ | —C(CH₃)=N—O—C₄H₉-n | H | H | CH₃ | CH | |
| 7.142 | OCH₃ | —C(CH₃)=N-3-CF₃-benzyloxy | H | H | H | CH | |
| 7.143 | OCH₃ | —C(CH₃)=N-3,CF₃-benzyloxy | H | H | CH₃ | CH | |
| 7.144 | OCH₃ | —C(CH₃)=N—O—CH(CH₃)—3-CF₃—Ph | H | H | H | CH | |
| 7.145 | OCH₃ | —C(CH₃)=N—O—CH(CH₃)—3-CF₃—Ph | H | H | CH₃ | CH | |
| 7.146 | OCH₃ | —C(CH₃)=N—O—(CH₂)₂—Ph | H | H | H | CH | |
| 7.147 | OCH₃ | —C(CH₃)=N—O—(CH₂)₂—Ph | H | H | CH₃ | CH | |
| 7.148 | OCH₃ | —C(CH₃)=N—O—(CH₂)₂—4-Cl—Ph | H | H | H | CH | |
| 7.149 | OCH₃ | —C(CH₃)=N—O—(CH₂)₂—4-Cl—Ph | H | H | CH₃ | CH | |
| 7.150 | OCH₃ | 3-Ph-5-CH₃-pyrazol-1-yl | H | H | H | CH | |
| 7.151 | OCH₃ | 3-Ph-5-CH₃-pyrazol-1-yl | H | H | CH₃ | CH | |
| 7.152 | OCH₃ | 3-Ph-1-CH₃-pyrazol-5-yl | H | H | H | CH | |
| 7.153 | OCH₃ | 3-Ph-1-CH₃-pyrazol-5-yl | H | H | CH₃ | CH | |
| 7.154 | OCH₃ | 3-CH₃-isoxazol-5-yl | H | H | CH₃ | CH | |
| 7.155 | OCH₃ | 3-CF₃-isoxazol-5-yl | H | H | H | CH | |
| 7.156 | OCH₃ | 3-CF₃-isoxazol-5-yl | H | H | CH₃ | CH | |
| 7.157 | OCH₃ | 3-Ph-isoxazol-5-yl | H | H | CH₃ | CH | |
| 7.158 | OCH₃ | 5-Ph-oxazol-2-yl | H | H | CH₃ | CH | |
| 7.159 | OCH₃ | C₃H₇-i | H | H | CH₃ | CH | |
| 7.160 | OCH₃ | CF₃ | H | H | CH₃ | CH | |
| 7.161 | OCH₃ | C₄H₉-n | H | H | CH₃ | CH | |
| 7.162 | OCH₃ | C₃H₇-i | H | CH₃ | CH₃ | CH | |
| 7.163 | OCH₃ | phenoxy | H | H | CH₃ | CH | |
| 7.164 | OCH₃ | 2-CH₃-phenoxy | H | H | CH₃ | CH | |
| 7.165 | OCH₃ | 2-CN-phenoxy | H | H | CH₃ | CH | |
| 7.166 | OCH₃ | 2-Cl-phenoxy | H | H | CH₃ | CH | |
| 7.167 | OCH₃ | 2-CH₃-benzyloxy | H | H | CH₃ | CH | |
| 7.168 | OCH₃ | 2-Cl-benzyloxy | H | H | CH₃ | CH | |
| 7.169 | OCH₃ | 3-Cl-benzyloxy | H | H | CH₃ | CH | |
| 7.170 | OCH₃ | 3-CF₃-benzyloxy | H | H | CH₃ | CH | |
| 7.171 | OCH₃ | —O—CH(CH₃)-3-CF₃—Ph | H | H | CH₃ | CH | |
| 7.172 | OCH₃ | —O—(CH₂)₂—Ph | H | H | CH₃ | CH | |
| 7.173 | OCH₃ | —O—CH₂—CH=CH—Ph | H | H | CH₃ | CH | |
| 7.174 | OCH₃ | —O—(CH₂)₃—Ph | H | H | CH₃ | CH | |
| 7.175 | OCH₃ | —O—(CH₂)₂—O—C₂H₅ | H | H | CH₃ | CH | |
| 7.176 | OCH₃ | —O—(CH₂)₂—O—Ph | H | H | CH₃ | CH | |
| 7.177 | OCH₃ | Ph | H | H | CH₃ | CH | |
| 7.178 | OCH₃ | 2-CH₂-benzyloxy | H | H | H | N | |
| 7.179 | OCH₃ | 2-Ph-thiazol-4-yl | H | H | H | N | |
| 7.180 | OCH₃ | —C(CH₃)=N-2-CH₃-benzyloxy | H | H | H | N | |
| 7.181 | OCH₃ | —C(CH₃)=N-3-Cl-benzyloxy | H | H | H | N | |
| 7.182 | OCH₃ | —C(CH₃)=N-3,4-Cl₂-benzyloxy | H | H | H | N | |
| 7.183 | OCH₃ | 2,5-(CH₃)₂—Ph | H | H | H | N | |
| 7.184 | OCH₃ | 3-C₄H₉-n-isoxazol-5-yl | H | H | H | N | |
| 7.185 | OCH₃ | 3-C₂H₅-isoxazol-5-yl | H | H | H | N | |
| 7.186 | OCH₃ | 3-C₃H₇-n-isoxazol-5-yl | H | H | H | N | |
| 7.187 | OCH₃ | —C(CH₃)=N—OCH₃ | H | H | H | N | |
| 7.188 | OCH₃ | —C(CH₃)=N—OCH₃ | H | H | CH₃ | N | |
| 7.189 | OCH₃ | —C(CH₃)=N—OC₂H₅ | H | H | H | N | |
| 7.190 | OCH₃ | —C(CH₃)=N—OC₂H₅ | H | H | CH₃ | N | |
| 7.191 | OCH₃ | —C(CH₃)=N-3-Cl-benzyloxy | H | H | CH₃ | N | |
| 7.192 | OCH₃ | Ph | H | H | CH₃ | N | |
| 7.193 | OCH₃ | CF₃ | H | H | H | N | |
| 7.194 | OCH₃ | CF₃ | H | H | CH₃ | N | |
| 7.195 | OCH₃ | C₃H₇-i | H | CH₃ | CH₃ | N | |

TABLE 7-continued

Compounds of formula II

| Comp. No. | R¹ | R² | R³ | R⁴ | R⁵ | X | physical data or ¹H-NMR |
|---|---|---|---|---|---|---|---|
| 7.196 | OCH₃ | 2-CH₃-phenoxy | H | H | CH₃ | N | |
| 7.197 | OCH₃ | 2-CN-phenoxy | H | H | H | N | |
| 7.198 | OCH₃ | 2-CN-phenoxy | H | H | CH₃ | N | |
| 7.199 | OCH₃ | 2-CH₃-benzyloxy | H | H | CH₃ | N | |
| 7.200 | OCH₃ | 3-CF₃-benzyloxy | H | H | CH₃ | N | |
| 7.201 | OCH₃ | —O—(CH₂)₂—Ph | H | H | H | N | |
| 7.202 | OCH₃ | —O—(CH₂)₂—Ph | H | H | CH₃ | N | |
| 7.203 | OCH₃ | 3-CF₃-isoxazol-5-yl | H | H | H | N | |
| 7.204 | OCH₃ | 3-CF₃-isoxazol-5-yl | H | H | CH₃ | N | |
| 7.205 | OCH₃ | 3-Ph-isoxazol-5-yl | H | H | CH₃ | N | |
| 7.206 | OCH₃ | 3-Ph-1-CH₃-pyrazol-5-yl | H | H | CH₃ | N | |
| 7.207 | OCH₃ | 2-Ph-thiazol-4-yl | H | H | H | N | |
| 7.208 | OCH₃ | 2-Ph-thiazol-4-yl | H | H | CH₃ | N | |
| 7.209 | OCH₃ | 5-Ph-oxazol-2-yl | H | H | CH₃ | N | |

TABLE 8

Compounds of formula III

| Comp. No. | R¹ | R² | R³ | R⁴ | R⁵ | physicial data or ¹H-NMR |
|---|---|---|---|---|---|---|
| 8.01 | OCH₃ | C₃H₇—i | H | H | H | |
| 8.02 | OCH₃ | CF₃ | H | H | H | |
| 8.03 | N(CH₃)₂ | Ph | H | H | H | |
| 8.04 | OCH₃ | CH₃ | H | H | H | 8.36(s, 1H);7.82–6.88(m, 4H);4.02(s, 3H);3.72(s, 2H);3.70(s, 3H);2.37(s, 3H). |
| 8.05 | N(CH₃)₂ | CN | H | H | H | |
| 8.06 | OCH₃ | Ph | H | H | H | |
| 8.07 | OCH₃ | CH₃ | CH₃ | H | H | |
| 8.08 | OCH₃ | C₄H₉—t | H | H | H | |
| 8.09 | N(CH₃)₂ | C₄H₉—t | H | H | H | 8.29(s, 1H);7.35–6.88(m, 4H);3.76(s, 2H);3.74(s, 3H);3.07(s, 6H);1.32(s, 9H). |
| 8.10 | OCH₃ | 2-CH₃—1,3-dioxolan-2-yl | H | H | H | 8.36(s, 1H);7.40–7.02(m, 4H);4.08–4.00 (m, 4H);4.02(s, 3H);3.82–3.74(m, 4H); 3.74(s, 2H);3.72(s, 3H);1.67(s, 3H). |
| 8.11 | N(CH₃)₂ | —C(CH₃)=N—O—CH₂—CH=CH₂ | H | H | H | |
| 8.12 | OCH₃ | —C(CH₃)=N—benzyloxy | H | H | H | |
| 8.13 | OCH₃ | 1,3-dioxan-2-yl | H | H | H | |
| 8.14 | —N—pyrrolidinyl | C₃H₇—i | H | H | H | |
| 8.15 | N(CH₃)₂ | phenoxy | H | H | H | |
| 8.16 | N(CH₃)₂ | Cl | H | H | H | |
| 8.17 | N(CH₃)₂ | —O—CH₂—CH=CH₂ | H | H | H | |
| 8.18 | N(CH₃)₂ | —O—CH₂—C≡CH | H | H | H | |
| 8.19 | N(CH₃)₂ | —O—CH₂CH=CH—CH₃ | H | H | H | |
| 8.20 | N(CH₃)₂ | —O—CH₂—CH=C(CH₃)₂ | H | H | H | |
| 8.21 | N(CH₃)₂ | benzyloxy | H | H | H | |
| 8.22 | N(CH₃)₂ | Cl | Cl | H | H | |
| 8.23 | N(CH₃)₂ | CH₃ | CH₃ | H | H | |
| 8.24 | OCH₃ | —O—CH₂—CH=CH₂ | H | H | H | |
| 8.25 | OCH₃ | —O—CH₂—CH=CH—CH₃ | H | H | H | |
| 8.26 | OCH₃ | —O—CH₂—C≡CH | H | H | H | |
| 8.27 | OCH₃ | —O—CH₂—CH=C(CH₃)₂ | H | H | H | |
| 8.28 | OCH₃ | 1,3-dioxolan-2-yl | H | H | H | |
| 8.29 | N(CH₃)₂ | 1,3-dioxan-2-yl | H | H | H | |
| 8.30 | N(CH₃)₂ | 2-CH₃—dioxolan-2-yl | H | H | H | |
| 8.31 | N(CH₃)₂ | 2,4,4-(CH₃)₃dioxolan-2-yl | H | H | H | |
| 8.32 | N(CH₃)₂ | CH₃ | H | H | H | |
| 8.33 | OCH₃ | C(CH₃)=CH₂ | H | H | H | |
| 8.34 | OCH₃ | C₃H₇—i | H | CH₃ | H | |
| 8.35 | OCH₃ | phenoxy | H | H | H | |
| 8.36 | OCH₃ | —O—CH₂—CH=CH—Ph | H | H | H | |
| 8.37 | OCH₃ | —O—(CH₂)₃—Ph | H | H | H | |
| 8.38 | OCH₃ | —O—(CH₂)₂—Ph | H | H | H | |
| 8.39 | OCH₃ | —O—(CH₂)₂—O—Ph | H | H | H | |
| 8.40 | OCH₃ | 2-CH₃—benzyloxy | H | CH₃ | CH₃ | |
| 8.41 | OCH₃ | 2-CH₃—phenoxy | H | H | H | |
| 8.42 | OCH₃ | 2-CN—phenoxy | H | H | H | 8.36(s, 1H);8.02–6.50(m, 8H);4.02(s, 3H);3.70(s, 5H). |
| 8.43 | OCH₃ | 2-Cl—phenoxy | H | H | H | |
| 8.44 | OCH₃ | 2-Ph—thiazol-4-yl | H | H | H | 8.38(s, 1H);8.09–7.08(m, 10H);4.02(s, 3H);3.79–3.70(2s, 8H). |

TABLE 8-continued

Compounds of formula III

| Comp. No. | R¹ | R² | R³ | R⁴ | R⁵ | physicial data or ¹H-NMR |
|---|---|---|---|---|---|---|
| 8.45 | OCH$_3$ | 3-Ph—isoxazol-5-yl | H | H | H | |
| 8.46 | OCH$_3$ | 1-CH$_3$—3-Ph—pyrazol-5-yl | H | H | H | |
| 8.47 | OCH$_3$ | 5-Ph—oxazol-2-yl | H | H | H | |
| 8.48 | OCH$_3$ | 3-CF$_3$—benzyloxy | H | H | H | |
| 8.49 | OCH$_3$ | —O—(CH$_2$)$_2$—O—C$_2$H$_5$ | H | H | H | |
| 8.50 | OCH$_3$ | —C(CH$_3$)=N—O—C$_2$H$_5$ | H | H | H | |
| 8.51 | OCH$_3$ | —C(CH$_3$)=N—3-Cl—benzyloxy | H | H | H | |
| 8.52 | OCH$_3$ | C$_3$H$_7$—i | H | CH$_3$ | CH$_3$ | |
| 8.53 | N(CH$_3$)$_2$ | C$_3$H$_7$—i | H | H | CH$_3$ | 7.28–6.82(m, 4H);3.84(s, 3H);3.78(s, 2H);3.02(s, 6H);2.89(dq, 1H);2.37(s, 3H);1.23(d, 6H). |
| 8.54 | OCH$_3$ | C$_3$H$_7$—i | H | H | CH$_3$ | 7.28–6.82(m, 4H);4.02(s, 3H);3.72(s, 2H);3.70(s, 3H);2.98(dq, 1H);2.32(s, 3H);1.22(d, 6H). |
| 8.55 | OCH$_3$ | CF$_3$ | H | H | CH$_3$ | |
| 8.56 | N(CH$_3$)$_2$ | Ph | H | H | CH$_3$ | |
| 8.57 | OCH$_3$ | C(CH$_3$)=NOCH$_3$ | H | H | CH$_3$ | |
| 8.58 | N(CH$_3$)$_2$ | C$_3$H$_7$—i | H | CH$_3$ | CH$_3$ | |
| 8.59 | OCH$_3$ | 2-CH$_3$—benzyloxy | H | H | CH$_3$ | |
| 8.60 | OCH$_3$ | —O—(CH$_2$)$_2$—Ph | H | H | CH$_3$ | |
| 8.61 | OCH$_3$ | 2-Ph—thiazol-4-yl | H | H | CH$_3$ | |
| 8.62 | OCH$_3$ | 3-CF$_3$—isoxazol-5-yl | H | H | CH$_3$ | |
| 8.63 | OCH$_3$ | 3-CH$_3$—isoxazol-5-yl | H | H | CH$_3$ | |
| 8.64 | N(CH$_3$)$_2$ | —C(CH$_3$)=N—4-Cl—benzyloxy | H | H | H | |
| 8.65 | N(CH$_3$)$_2$ | —C(CH$_3$)=N—benzyloxy | H | H | H | |
| 8.66 | N(CH$_3$)$_2$ | —C(CH$_3$)=N—3-Cl—benzyloxy | H | H | H | |
| 8.67 | N(CH$_3$)$_2$ | —C(CH$_3$)=N—O—C$_2$H$_5$ | H | H | H | |
| 8.68 | N(CH$_3$)$_2$ | CF$_3$ | H | H | H | |
| 9.69 | N(CH$_3$)$_2$ | —C(CH$_3$)=N—OCH$_3$ | H | H | H | |
| 8.70 | N(CH$_3$)$_2$ | —C(CH$_3$)=N—O—CH$_2$—C(CH$_3$)=CH$_2$ | H | H | H | |
| 8.71 | N(CH$_3$)$_2$ | —C(CH$_3$)=N—OCH$_3$ | H | H | CH$_3$ | |
| 8.72 | N(CH$_3$)$_2$ | C$_4$H$_9$—t | H | H | CH$_3$ | |
| 8.73 | N(CH$_3$)$_2$ | 3,4-(OCH$_3$)$_2$—Ph | H | H | CH$_3$ | |
| 8.74 | N(CH$_3$)$_2$ | 4-OCH$_3$—Ph | H | H | CH$_3$ | |
| 8.75 | N(CH$_3$)$_2$ | 3,5-(CH$_3$)$_2$—pyrazol-1-yl | H | H | CH$_3$ | |
| 8.76 | N(CH$_3$)$_2$ | 3-CH$_3$—isoxazol-5-yl | H | H | CH$_3$ | |
| 8.77 | N(CH$_3$)$_2$ | 2-CH$_3$—phenoxy | H | H | CH$_3$ | |
| 8.78 | N(CH$_3$)$_2$ | 2-Cl—phenoxy | H | H | CH$_3$ | |
| 8.79 | N(CH$_3$)$_2$ | 2-CN—phenoxy | H | H | H | |
| 8.80 | N(CH$_3$)$_2$ | 2-CH$_3$—benzyloxy | H | H | CH$_3$ | |
| 8.81 | N(CH$_3$)$_2$ | 2,4—Cl$_2$—benzyloxy | H | H | CH$_3$ | |
| 8.82 | N(CH$_3$)$_2$ | —O—(CH$_2$)$_2$—Ph | H | H | CH$_3$ | |
| 8.83 | N(CH$_3$)$_2$ | 2-Ph—thiazol-4-yl | H | H | CH$_3$ | |
| 8.84 | N(CH$_3$)$_2$ | 3-CF$_3$—isoxazol-5-yl | H | H | CH$_3$ | |
| 8.85 | N(CH$_3$)$_2$ | —C(CH$_3$)=N—O—C$_3$H$_7$—i | H | H | H | |
| 8.86 | N(CH$_3$)$_2$ | —C(CH$_3$)=N—O—C$_3$H$_7$—i | H | H | CH$_3$ | |
| 8.87 | N(CH$_3$)$_2$ | —C(CH$_3$)=N—O—C$_4$H$_9$—n | H | H | H | |
| 8.88 | N(CH$_3$)$_2$ | —C(CH$_3$)=N—O—C$_4$H$_9$—n | H | H | CH$_3$ | |
| 8.89 | N(CH$_3$)$_2$ | —C(CH$_3$)=N—O—CH$_2$—C(CH$_3$)=CH$_2$ | H | H | H | |
| 8.90 | N(CH$_3$)$_2$ | —C(CH$_3$)=N—O—CH$_2$—CH=CH$_2$ | H | H | CH$_3$ | |
| 8.91 | N(CH$_3$)$_2$ | —C(CH$_3$)=N—O—CH$_2$—C≡CH | H | H | H | |
| 8.92 | N(CH$_3$)$_2$ | —C(CH$_3$)=N—O—CH$_2$—C≡CH | H | H | CH$_3$ | |
| 8.93 | N(CH$_3$)$_2$ | —C(CH$_3$)=N—O—C$_2$H$_5$ | H | H | CH$_3$ | |
| 8.94 | N(CH$_3$)$_2$ | —C(CH$_3$)=N—benzyloxy | H | H | CH$_3$ | |
| 8.95 | N(CH$_3$)$_2$ | —C(CH$_3$)=N—3-Cl—benzyloxy | H | H | CH$_3$ | |
| 8.96 | N(CH$_3$)$_2$ | —C(CH$_3$)=N—4-Cl—benzyloxy | H | H | CH$_3$ | |
| 8.97 | N(CH$_3$)$_2$ | —C(CH$_3$)=N—2-Cl—benzyloxy | H | H | CH$_3$ | |
| 8.98 | N(CH$_3$)$_2$ | —C(CH$_3$)=N—2-CH$_3$—benzyloxy | H | H | CH$_3$ | |
| 8.99 | N(CH$_3$)$_2$ | —C(CH$_3$)=N—2,5-(CH$_3$)$_2$—benzyloxy | H | H | CH$_3$ | |
| 8.100 | N(CH$_3$)$_2$ | —C(CH$_3$)=N—O—CH(CH$_3$)—3-CF$_3$—Ph | H | H | CH$_3$ | |
| 8.101 | N(CH$_3$)$_2$ | —C(CH$_3$)=N—3-CF$_3$—benzyloxy | H | H | CH$_3$ | |
| 8.102 | N(CH$_3$)$_2$ | —C(CH$_3$)=N—3-CF$_3$—benzyloxy | H | H | H | |
| 8.103 | N(CH$_3$)$_2$ | —C(CH$_3$)=N—O—(CH$_2$)$_2$—3-Cl—Ph | H | H | CH$_3$ | |
| 8.104 | N(CH$_3$)$_2$ | —C(CH$_3$)=N—O—(CH$_2$)$_2$—4-Cl—Ph | H | H | CH$_3$ | |
| 8.105 | N(CH$_3$)$_2$ | 3-Ph—5-CH$_3$—pyrazol-1-yl | H | H | CH$_3$ | |
| 8.106 | N(CH$_3$)$_2$ | 3-Ph—isoxazol-5-yl | H | H | CH$_3$ | |
| 8.107 | N(CH$_3$)$_2$ | 3-Ph—1-CH$_3$—pyrazol-5-yl | H | H | CH$_3$ | |
| 8.108 | N(CH$_3$)$_2$ | 3-CF$_3$—1-CH$_3$—pyrazol-5-yl | H | H | CH$_3$ | |
| 8.109 | N(CH$_3$)$_2$ | 5-CH$_3$—oxazol-2-yl | H | H | CH$_3$ | |
| 8.110 | N(CH$_3$)$_2$ | 5-Ph—oxazol-2-yl | H | H | CH$_3$ | |
| 8.111 | N(CH$_3$)$_2$ | 5-CF$_3$—oxazol-2-yl | H | H | CH$_3$ | |
| 8.112 | N(CH$_3$)$_2$ | 3-CF$_3$—benzyloxy | H | H | CH$_3$ | |
| 8.113 | N(CH$_3$)$_2$ | —O—CH(CH$_3$)—3-CF$_3$—Ph | H | H | CH$_3$ | |
| 8.114 | N(CH$_3$)$_2$ | —O—(CH$_2$)$_2$—OCH$_3$ | H | H | CH$_3$ | |

TABLE 8-continued

Compounds of formula III

| Comp. No. | R¹ | R² | R³ | R⁴ | R⁵ | physical data or ¹H-NMR |
|---|---|---|---|---|---|---|
| 8.115 | N(CH₃)₂ | —O—(CH₂)₂—O—C₂H₅ | H | H | CH₃ | |
| 8.116 | N(CH₃)₂ | —O—(CH₂)₂—O—C₄H₉—n | H | H | CH₃ | |
| 8.117 | N(CH₃)₂ | —O—(CH₂)₂—O—Ph | H | H | CH₃ | |
| 8.118 | OCH₃ | 2-CH₃—benzyloxy | H | H | H | 8.39(s, 1H);7.42–6.70(m, 8H);5.01(s, 2H);4.05(s, 3H);3.70(s, 5H);2.35(s, 3H). |
| 8.119 | OCH₃ | 3-NO₂—Ph | H | H | H | 8.45–7.09(m, 10H);4.02(s, 3H);3.72(s, 2H);3.70(s, 3H). |
| 8.120 | OCH₃ | 3-Cl—benzyloxy | H | H | H | 8.39(s, 1H);7.44–6.70(m, 8H);5.02(s, 2H);4.02(s, 3H);3.70(s, 5H). |
| 8.121 | OCH₃ | —O—(CH₂)₂—Ph | H | H | H | 8.35(s, 1H);7.39–6.60(m, 9H);4.15(t, 2H); 4.04(s, 3H);3.72(s, 3H);3.11(t, 2H). |
| 8.122 | OCH₃ | 2,5-(CH₃)₂—Ph | H | H | H | 8.39(s, 1H);7.49–7.02(m, 7H);4.02(s, 3H);3.75(s, 2H);3.72(s, 3H);2.35(s, 3H); 2.28(s, 3H). |
| 8.123 | OCH₃ | 3-C₂H₅—isoxazol-5-yl | H | H | H | 8.39(s, 1H);7.68–7.12(m, 4H);6.40(s, 1H);4.02(s, 3H);3.74(s, 2H);3.72(s, 3H); 2.75(s, 2H);1.34(t, 3H). |
| 8.124 | OCH₃ | 3-C₄H₉—n-isoxazol-5-yl | H | H | H | 8.39(s, 1H);8.04–7.15(m, 5H);6.40(s, 1H);4.05(s, 3H);3.78(s, 2H);3.76(s, 3H). |
| 8.125 | OCH₃ | 2-CN—phenoxy | H | H | H | |
| 8.126 | OCH₃ | 2-naphthyl | H | H | H | 8.39(s, 1H);8.05–7.10(m, 11H);4.02(s, 3H);3.78(s, 2H);3.75(s, 3H);2.70(t, 2H); 1.82–1.58(m, 2H);1.02(t, 3H). |
| 8.127 | OCH₃ | 2-Ph—thiazol-4-yl | H | H | H | 8.39(s, 1H);8.09–7.10(m, 10H);4.02(s, 3H);3.75(s, 2H);3.73(s, 3H). |
| 8.128 | OCH₃ | —C(CH₃)=N—3,4-Cl₂—benzyloxy | H | H | H | |
| 8.129 | OCH₃ | —C(CH₃)=N—2-Cl—benzyloxy | H | H | H | 8.35(s, 1H);7.52–7.18(m, 8H);5.20(s, 2H);4.05(s, 3H);3.76(s, 2H);3.75(s, 3H); 2.25(s, 2H). |
| 8.130 | OCH₃ | —C(CH₃)=N—2-CH₃—benzyloxy | H | H | H | 8.35(s, 1H);7.54–7.08(m, 8H);5.25(s, 2H);4.02(s, 3H);3.75(s, 2H);3.73(s, 3H); 2.41(s, 3H);2.25(s, 3H). |
| 8.131 | OCH₃ | 2-Cl—benzyloxy | H | H | H | 8.39(s, 1H);7.60–6.40(m, 8H);5.14(s, 2H);4.02(s, 3H);3.72(s, 5H). |
| 8.132 | OCH₃ | —C(CH₃)=N—OCH₃ | H | H | H | |
| 8.133 | OCH₃ | —C(CH₃)=N—O—C₃H₇—i | H | H | H | 8.38(s, 1H);7.71–6.74(m, 5H);4.04(s, 3H);3.75(s, 2H);3.73(s, 3H). |
| 8.134 | OCH₃ | —C(CH₃)=N—O—C₃H₇—i | H | H | CH₃ | 7.70–7.00(m, 5H);4.01(s, 3H);3.70(s, 3H);3.68(s, 2H);7.40(s, 3H). |
| 8.135 | OCH₃ | —C(CH₃)=N—O—C₄H₉—n | H | H | H | |
| 8.136 | OCH₃ | —C(CH₃)=N—O—C₄H₉—n | H | H | CH₃ | |
| 8.137 | OCH₃ | —C(CH₃)=N—3-CF₃—benzyloxy | H | H | H | |
| 8.138 | OCH₃ | —C(CH₃)=N—3,CF₃—benzyloxy | H | H | CH₃ | |
| 8.139 | OCH₃ | —C(CH₃)=N—O—CH(CH₃)—3-CF₃—Ph | H | H | H | |
| 8.140 | OCH₃ | —C(CH₃)=N—O—CH(CH₃)—3-CF₃—Ph | H | H | CH₃ | |
| 8.141 | OCH₃ | —C(CH₃)=N—O—(CH₂)₂—Ph | H | H | H | |
| 8.142 | OCH₃ | —C(CH₃)=N—O—(CH₂)₂—Ph | H | H | CH₃ | |
| 8.143 | OCH₃ | —C(CH₃)=N—O—(CH₂)₂—4-Cl—Ph | H | H | H | |
| 8.144 | OCH₃ | —C(CH₃)=N—O—(CH₂)₂—4-Cl—Ph | H | H | CH₃ | |
| 8.145 | OCH₃ | 3-Ph—5-CH₃—pyrazol-1-yl | H | H | H | |
| 8.146 | OCH₃ | 3-Ph—5-CH₃—pyrazol-1-yl | H | H | CH₃ | |
| 8.147 | OCH₃ | 3-Ph—1-CH₃—pyrazol-5-yl | H | H | H | |
| 8.148 | OCH₃ | 3-Ph—1-CH₃—pyrazol-5-yl | H | H | CH₃ | |
| 8.149 | OCH₃ | 3-CH₃—isoxazol-5-yl | H | H | CH₃ | |
| 8.150 | OCH₃ | 3-CF₃—isoxazol-5-yl | H | H | H | 8.38(s, 1H);7.71–6.74(m, 5H);4.04(s, 3H);3.75(s, 2H);3.73(s, 3H). |
| 8.151 | OCH₃ | 3-CF₃—isoxazol-5-yl | H | H | CH₃ | 7.70–7.00(m, 5H);4.05(s, 3H);3.70(s, 3H);3.68(s, 2H);2.40(s, 3H). |
| 8.152 | OCH₃ | 3-Ph—isoxazol-5-yl | H | H | CH₃ | |
| 8.153 | OCH₃ | 5-Ph—oxazol-2-yl | H | H | CH₃ | |
| 8.154 | OCH₃ | C₃H₇—i | H | H | CH₃ | |
| 8.155 | OCH₃ | CF₃ | H | H | CH₃ | |
| 8.156 | OCH₃ | C₄H₉—n | H | H | CH₃ | |
| 8.157 | OCH₃ | C₃H₇—i | H | CH₃ | CH₃ | |
| 8.158 | OCH₃ | phenoxy | H | H | CH₃ | |
| 8.159 | OCH₃ | 2-CH₃—phenoxy | H | H | CH₃ | |
| 8.160 | OCH₃ | 2-CN—phenoxy | H | H | CH₃ | |
| 8.161 | OCH₃ | 2-Cl—phenoxy | H | H | CH₃ | |
| 8.162 | OCH₃ | 2-CH₃—benzyloxy | H | H | CH₃ | |
| 8.163 | OCH₃ | 2-Cl—benzyloxy | H | H | CH₃ | |
| 8.164 | OCH₃ | 3-Cl—benzyloxy | H | H | CH₃ | |
| 8.165 | OCH₃ | 3-CF₃—benzyloxy | H | H | CH₃ | |
| 8.166 | OCH₃ | —O—CH(CH₃)—3-CF₃—Ph | H | H | CH₃ | |
| 8.167 | OCH₃ | —O—(CH₂)₂—Ph | H | H | CH₃ | |

TABLE 8-continued

Compounds of formula III

| Comp. No. | $R^1$ | $R^2$ | $R^3$ | $R^4$ | $R^5$ | physical data or $^1$H-NMR |
|---|---|---|---|---|---|---|
| 8.168 | OCH$_3$ | —O—CH$_2$—CH=CH—Ph | H | H | CH$_3$ | |
| 8.169 | OCH$_3$ | —O—(CH$_2$)$_3$—Ph | H | H | CH$_3$ | |
| 8.170 | OCH$_3$ | —O—(CH$_2$)$_2$—O—C$_2$H$_5$ | H | H | CH$_3$ | |
| 8.171 | OCH$_3$ | —O—(CH$_2$)$_2$—O—Ph | H | H | CH$_3$ | |
| 8.172 | OCH$_3$ | Ph | H | H | CH$_3$ | |
| 8.173 | OCH$_3$ | —C(CH$_3$)=N—2-CH$_3$—benzyloxy | H | H | H | |
| 8.174 | OCH$_3$ | 3-C$_3$H$_7$—n-isoxazol-5-yl | H | H | H | 8.39(s, 1H);7.39–7.15(m, 4H);6.40(s, 1H);4.05(s, 3H);3.72(s, 5H);2.70(t, 2H); 1.72(m, 2H);1.05(t, 3H). |
| 8.175 | OCH$_3$ | —C(CH$_3$)=N—OC$_2$H$_5$ | H | H | CH$_3$ | |
| 8.176 | OCH$_3$ | —C(CH$_3$)=N—3-Cl—benzyloxy | H | H | CH$_3$ | 7.50–7.02(m, 8H);5.20(s, 2H);4.00(s, 3H);3.68(s, 3H);3.65(s, 2H);2.42(s, 3H); 2.29(s, 3H). |

TABLE 9

Compounds of formula IV

| Comp. No. | $R^1$ | $R^5$ | physical data |
|---|---|---|---|
| 9.01 | OCH$_3$ | H | m.p. 64° C. |
| 9.02 | N(CH$_3$)$_2$ | H | m.p. 30–32° C. |
| 9.03 | OCH$_3$ | CH$_3$ | b.p. 108–110° C./0.5 torr |
| 9.04 | N(CH$_3$)$_2$ | CH$_3$ | b.p. 140–144° C./0.5 torr |

TABLE 10

Compounds of formula VI

| Comp. No. | $R^5$ | physical data |
|---|---|---|
| 10.01 | H | m.p. 65–67° C. |
| 10.02 | CH$_3$ | m.p. 70–72° C. |

TABLE 11

Compounds of formula VIII

| Comp. No. | $R^5$ | physical data |
|---|---|---|
| 11.01 | H | m.p. >200° C. |
| 11.02 | CH$_3$ | m.p. >200° C. |

TABLE 12

Compounds of formula X

| Comp. No. | $R^1$ | $R^3$ | $R^4$ | $R^5$ | $R_7$ | physical data or $^1$H—NMR |
|---|---|---|---|---|---|---|
| 12.01 | OCH$_3$ | H | H | H | CH$_3$ | m.p. 65–67° C. |
| 12.02 | N(CH$_3$)$_2$ | H | H | H | CH$_3$ | 8.26(s, 1H);7.82–7.25(m, 4H);3.77 (s, 2H);3.75(s, 3H);3.08(s, 6H); 2.60(s, 3H). |
| 12.03 | OCH$_3$ | H | H | H | C$_2$H$_5$ | |
| 12.04 | OCH$_3$ | H | H | CH$_3$ | CH$_3$ | |
| 12.05 | N(CH$_3$)$_2$ | H | H | CH$_3$ | CH$_3$ | 7.84–7.20(m, 4H);3.78(s, 2H);3.75 (s, 3H);3.06(s, 6H);2.60(s, 3H); 2.37(s, 3H). |

Biological activity is determinated according to the following examples

Example A: Activity against Powdery Mildew
*Sphaerotheca fuliginea*

Plants of Cucumis sativus (cucumber), 7 days old (cotyledon stage), are sprayed to near run off with a suspension containing 100 mg/l of active ingredient. The deposit is then allowed to dry. One day later, the treated plants are inoculated with a spore suspension containing 1×10$^5$ /ml of freshly collected conidia of *Sphaerotheca fuliginea* and then incubated in the greenhouse for 7 days at +24° C. and 60% r.h.

The efficacy of the test compounds is determined by comparing the degree of fungal attack with that on untreated, similarly inoculated check plants. In this test compounds 1.03, 1.04, 1.11, 1.40, 2.04, 2.06, 3.02, 3.03, 3.04, 3.05, 3.06 and 3.13, showed an efficacy of more than 90%.

Similar methods are used to test the compounds against the following pathogens:

*Podosphaera leucotricha* on apple,
*Erysiphe graminis* on wheat and barley (dry inoculation),
*Uncinula necator* on grape.

Example B: Activity against Rust, Scab, Pyrenophora, Leptosphaeria
*Uromyces appendiculatus:*

Plants of *Phaseolus vulgaris* (pole bean), 14 days old (2 leaves stage), are sprayed to near run off with a suspension containing 100 mg/l of the active ingredient. The deposit is then allowed to dry. One day later, the treated plants are inoculated with a spore suspension containing 1×10$^5$/ml of freshly collected spores of Uromyces appendiculatus. Incubation is performed for 3 days in a high humidity cabinet at +23° C. and >95% r.h. and thereafter during 10 days at +24° C. and 60% r.h.

The efficacy the compounds is determined by comparing the degree of fungal attack with that on untreated, similarly inoculated check plants. In this test compounds 1.3, 1.11 and 1.40, 2.04, 2.06, 3.01, 3.02, 3.03, 3.04, 3.05, 3.06, 3.12, 3.13, 4.09 and 4.10 showed an efficacy of at least 90%.

Similar methods are used to test the compounds against the following pathogens: *Puccinia triticina* on wheat (plants 10 days old),

*Pyrenophora graminea* on barley,

*Leptosphaeria nodorum* on wheat,

*Venturia inaequalis* on apple (plants 21 days old; the spore suspension contains 1% malt).

Example C: Activity against Downy Mildew

Plants of *Lycopersicon esculentum* (tomato) with 6 leaves, are sprayed to near run off with a spray suspension containing 500 mg/l of the active ingredient. The deposit is then allowed to dry. 1 day later, the treated plants are inoculated with a spore suspension containing 1×10⁵/ml of freshly collected sporangia of *Phytophthora_infestans* and then incubated for 7 days in a high humidity cabinet at +18° C. and >95 % r.h. The efficacy of the test compounds is determined by comparing the degree of fungal attack with that on untreated, similarly inoculated check plants. In this test compounds 1.40 and 3.08 showed an efficacy of at least 90%.

A similar method is used to test the compounds against Plasmopara viticola on grape vine.

Example D: Activity after Seed Treatment

The compounds of the invention may also be used for seed treatment. The advantageous fungicidal activity is established by in vitro tests with the following pathogens:

*Pyrenophora graminea*,

*Ustilago nuda*,

*Gerlachia nivalis*,

*Leptoshpaeria nodorum*.

Autoclaved wheat seeds are inoculated with spores or mycelium of the pathogens and coated with different concentrations of the test compounds resulting in dosages of 50 g a.i./100 kg seed. The treated seeds are then placed on agar plates and the pathogens allowed to grow for 3–8 days at +24° C. in the dark.

The efficacy of the test compounds is determined by comparing the degree of fungal growth emerging from treated and untreated inoculated seeds.

To evaluate the crop plant tolerance of the compounds, healthy seeds of wheat and barley are coated with the dosages mentioned above. The seeds are then allowed to germinate in petri dishes on moist filter paper in high humidity at +18° C. for 10 days. Plant damage is recorded, comparing the growth of treated and untreated seedlings.

In this test compounds 1.41 showed an efficacy of at least 90% against *Pyrenophora graminea*.

We claim:

1. 2-(4-Phenoxypyrimidin-5-yl)-acrylic acid derivatives of formula I

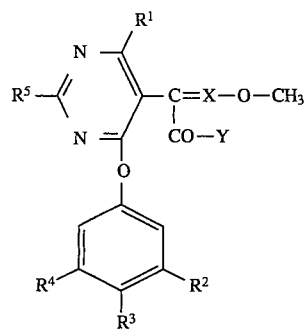

wherein $R^1$ is $C_{1-4}$alkoxy or $-NR^8R^9$, $R^2$ is $C_{1-4}$alkyl, $C_{1-4}$haloalkyl, aryl, aryloxy, $C_{3-5}$alkenyloxy, $C_{3-5}$alkynyloxy, halogen, aryl-$C_{1-4}$alkoxy, aryloxy-$C_{1-4}$alkyl, aryloxy-$C_{1-4}$alkoxy, aryl-$C_{3-5}$alkenyloxy, $C_{1-4}$alkoxy, $C_{2-5}$alkenyl, $C_{2-5}$alkynyl, $C_{1-4}$alkoxycarbonyl, -CONR¹⁰R¹¹, -O-CONR¹⁰R¹¹, -CR⁷=N-NR⁶R¹², or -CRT⁷=N-O-R⁶

$R^3$ is hydrogen, $C_{1-4}$alkyl; $C_{1-4}$alkoxy, cyano, nitro or halogen, $R^4$ is hydrogen, halogen, $C_{1-4}$alkoxy or $C_{1-4}$alkyl, $R^5$ is hydrogen or methyl, $R^6$ is $C_{1-12}$alkenyl, $C_{3-12}$alkellyl, $C_{3-12}$alkynyl, aryl-$C_{1-4}$alkyl, or aryl, $R^7$ is hydrogen or methyl, $R^8$ and $R^9$ are independently $C_{1-4}$alkyl, $R^{10}$ and $R^{11}$ are independently $C_{1-4}$alkyl, $R^{12}$ is hydrogen or methyl, X is CH or nitrogen, and Y is $OCH_3$, $NH_2$, $NHCH_3$ or $N(CH_3)_2$.

2. Compounds according to claim 1, wherein $R^1$ is methoxy or dimethylamino.

3. Compounds according to claim 1 wherein $R^1$ is methoxy or dimethylamino, $R^2$ is phenyl, phenoxy, $C_{1-4}$alkyl, $-C(CH_3)=N-O-R^6$ or $CF_3$, $R^3$ is hydrogen, $R^4$ is hydrogen or methyl and $R^5$ is hydrogen or methyl, wherein $R^6$ is $C_{1-6}$alkyl, or allyl; or is benzyl or 2-phenylethyl each optionally substituted at the phenyl ring with $C_{1-4}$alkyl, $C_{1-4}$alkoxy, halogen or $CF_3$.

4. Compounds according to claim 1, wherein $R^3$ is hydrogen.

5. Compounds according to claim 1, wherein $R^4$ is hydrogen or methyl.

6. Compounds according to claim 1, wherein $R^5$ is hydrogen or methyl.

7. Compounds according to claim 1, wherein $R^2$ is phenyl, phenoxy, $C_{1-4}$alkyl, $-C(CH_3)=N-O-R^6$ or $CF_3$, wherein $R^6$ is $C_{1-6}$alkyl or allyl, or is benzyl or 2-phenylethyl, each optionally substituted at the phenyl ring with $C_{1-4}$alkyl, $C_{1-4}$alkoxy, halogen or $CF_3$.

8. A compound according to claim 1, selected from the group comprising

Methyl α-[4-(3-methyl-5-isopropylphenoxy)-6-methoxypyrimidin-5-yl]-β-methoxyacrylate;

Methyl α-[4-(3-tert.butylphenoxy)-6-methoxy-pyrimidin-5-yl]-β-methoxyacrylate;

Methyl α-[4-(3-tert.butylphenoxy)-6-dimethylaminopirimidin-5-yl]-β-methoxyacrylate;

Methyl α-[4-(3-isopropylphenoxy)-6-methoxy-pyrimidin-5-yl]-β-methoxyacrylate;

Methyl α-[4-(3-trifluoromethylphenoxy)-6-methoxy-pyrimidin-5-yl]-β-methoxyacrylate;

Methyl 2-[4-(3-phenoxyphenoxy)-6-methoxy-pyrimidin-5-yl]-β-methoxyacrylate;

Methyl 2-[4-(3-(1-(3-chlorobenzyloximino)-ethyl)-phenoxy)-6-dimethylamino-pyrimidin-5-yl]- 2-methoximino-acetate;

Methyl-2-[4-(3-(1-ethoximino )-ethyl)-phenoxy)-6-dimethylamino-pyrimidin-5-yl]- 2-methoximino-acetate;

Methyl α-[4-(3-(1-methoximino)-ethyl)-phenoxy)-6-methoxy-2-methyl-pyrimidin-5-yl]-β-methoxyacrylate;

Methyl α- [4-(3-trifluoremethylphenoxy)-6-methoxy-2-methyl-pyrimidin-5-yl]-β-methoxy-acrylate;

Methyl 2-[4-(3-(1-ethoximino)-ethyl)-phenoxy)-6-dimethylamino-2-methyl-pirimidin-5-yl]- 2-methoximino-acetate;

Methyl 2-[4-(3-(1-(2,5-dimethylbenzyloximino)-ethyl)-phenoxy)- 6-dimethylamino-pyrimidin-5-methoximino-acetate;

Methyl 2-[4-(3-(1-(3-chlorobenzyloximino)-ethyl)-phenoxy)-6-dimethylamino- 2-methyl- pyrimidin]-2-methoximino-acetate; .

Methyl 2-[4-(3-(1-(2,5-dimethylbenzyloximino)-ethyl)-phenoxy)- 6-dimethylamino-2-methyl-pyrimidin-5-yl]-2-methoximino-acetate;

Methyl 2-[4-(3-(1-(2,5-dichlorobenzyloximino)-ethyl)-phenoxy)- 6-dimethylamino-2-methyl-pyrimidin-5-yl] -2-methoximino-acetate;

Methyl α-[4-(3-(1-(2,5-dimethylbenzyloximino)-ethyl)-phenoxy)-6-methoxy- 2-methyl-pyrimidin-5-yl]-α-methoxyacrylate;

Methyl α-[4-( 3-(1-(3-chlorobenzyloximino)-ethyl)-phenoxy)-6-methoxy- 2-methyl-pyrimidin-5-methoxyacrylate;

Methyl α-[4-(3-(1-(2,5-dimethylbenzyloximino)-ethyl)-phenoxy)- 6-methoxy-pyrimidin-5-yl]-β-methoxyacrylate;

Methyl 2-[4-(3-(1-(3-chlorobenzyloximino)-ethyl)-phenoxy)- 6-methoxy-pyrimidin-5-yl]-2-methoximino-acetate;

Methyl 2- [4-(3-phenylphenoxy)-6-dimethylamino-pyrimidin- 5-yl]-2-methoximino-acetate;

Methyl 2-[4-(5-methyl-3-isopropyl-phenoxy)- 6-dimethylamino-pyrimidin-5-yl]-2-methoximino-acetate;

Methyl 2-[4-(5-methyl-3-isopropyl-phenoxy)-6-dimethylamino- 2-methyl-pyrimidin-5-yl]-2-methoximido-acetate;

Methyl 2-[4-(3-(2-methylbenzyloxy)-phenoxy)-6-dimethylamino-pyrimidin- 5-yl]-2-methoximino-acetate;

Methyl 2-[4-(3-(2-methylbenzyloxy)-phenoxy)-6-dimethylamino-2-methyl-pyrimidin- 5-yl]-2-methoximino-acetate;

Methyl 2-[4-(3-phenylethoxy-phenoxy)-6-dimethylamino- 2-methyl-pyrimidin-5- yl]-2-methoximino-acetate;

Methyl 2-[4-(3-phenylethoxy)-phenoxy)-6-dimethylamino- 2-methyl-pyrimidin-5-yl]-2-methoximino-acetate;

Methyl 2-[4-(3-phenylphenoxy)-6-dimethylamino-2-methyl-pyrimidin- 5-yl]-2-methoximino-acetate;

N-methyl 2-[4-(3-phenylphenoxy)-6-dimethylamino-2-methyl-pyrimidin-5-yl]- 2-methoximino-acetamide;

Methyl α-[4-(3-phenylphenoxy)-6-dimethylamino-2-methyl-pyrimidin- 5-yl]-β-methoxy-acrylate;

Methyl α-[4-(5-methyl-3-isopropylphenoxy)-6-methoxy-2-methylpyrimidin- 5-yl]β-methoxy-acrylate; and Methyl α-[4-(3-(2-methylphenoxy)-phenoxy)-6-methoxy-2-methylpyrimidin- 5-yl]-methoxy-acrylate.

9. Method of combatting phytopathogenic fungi comprising applying to the fungi or their habitat a fungicidally effective amount of a compound of formula I according to claim 1.

10. Fungicidal composition comprising a compound of formula I stated in claim 1 and a agriculturally acceptable diluent.

11. Compounds of formula II

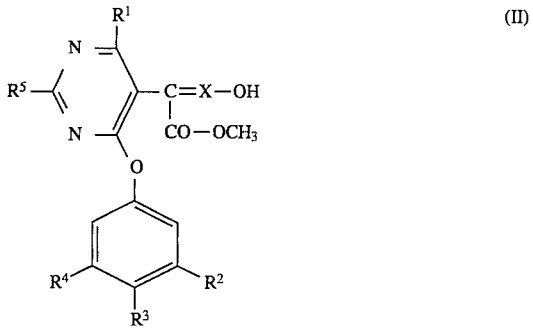

wherein $R^1$, $R^2$, $R^3$, $R^4$, $R^5$ and X are as defined in claim 1.

* * * * *